US007361680B2

(12) United States Patent
Carson et al.

(10) Patent No.: US 7,361,680 B2
(45) Date of Patent: Apr. 22, 2008

(54) INDOLE COMPOUNDS USEFUL FOR THE TREATMENT OF CANCER

(75) Inventors: Dennis A. Carson, La Jolla, CA (US); Howard B. Cottam, Escondido, CA (US); Lorenzo M. Leoni, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 11/467,472

(22) Filed: Aug. 25, 2006

(65) Prior Publication Data

US 2006/0293253 A1 Dec. 28, 2006

Related U.S. Application Data

(60) Division of application No. 11/013,955, filed on Dec. 16, 2004, now Pat. No. 7,129,262, which is a continuation-in-part of application No. 09/634,207, filed on Aug. 9, 2000, now Pat. No. 7,151,100, which is a continuation-in-part of application No. 09/360,020, filed on Jul. 23, 1999, now Pat. No. 6,545,034.

(51) Int. Cl.
*A61K 31/407* (2006.01)
*C07D 471/04* (2006.01)

(52) U.S. Cl. ...................... 514/411; 548/429

(58) Field of Classification Search ............... None
See application file for complete search history.

(56) References Cited

U.S. PATENT DOCUMENTS

| | | | |
|---|---|---|---|
| 3,053,255 A | 9/1962 | Meyer |
| 3,710,795 A | 1/1973 | Higuchi et al. |
| 3,843,480 A | 10/1974 | Dreher |
| 3,843,681 A | 10/1974 | Demerson et al. |
| 3,939,178 A | 2/1976 | Demerson et al. |
| 3,948,254 A | 4/1976 | Zaffaroni |
| 3,948,262 A | 4/1976 | Zaffaroni |
| 3,974,179 A | 8/1976 | Demerson et al. |
| 3,993,073 A | 11/1976 | Zaffaroni |
| 4,041,169 A | 8/1977 | Demerson et al. |
| 4,179,503 A | 12/1979 | Asselin et al. |
| 4,310,509 A | 1/1982 | Berglund et al. |
| 4,337,760 A | 7/1982 | Rubin |
| 4,460,562 A | 7/1984 | Keith et al. |
| 4,466,953 A | 8/1984 | Keith et al. |
| 4,482,534 A | 11/1984 | Blank |
| 4,485,097 A | 11/1984 | Bell |
| 4,505,891 A | 3/1985 | Ito |
| 4,533,540 A | 8/1985 | Blank |
| 4,542,012 A | 9/1985 | Dell |
| 4,542,013 A | 9/1985 | Keith et al. |
| 4,560,555 A | 12/1985 | Snider |
| 4,585,877 A | 4/1986 | Demerson et al. |
| 4,597,961 A | 7/1986 | Etscorn |
| 4,608,249 A | 8/1986 | Otsuka |
| 4,686,213 A | 8/1987 | Ferdinandi et al. |
| 4,748,252 A | 5/1988 | Ferdinandi et al. |
| 4,806,356 A | 2/1989 | Shaw |
| 4,940,587 A | 7/1990 | Jenkins et al. |
| 5,561,151 A | 10/1996 | Young et al. |
| 5,599,946 A | 2/1997 | Vincenzo et al. |
| 5,776,967 A | 7/1998 | Kreft et al. |
| 5,780,435 A | 7/1998 | Garnick et al. |
| 5,811,558 A | 9/1998 | Adger et al. |
| 5,824,699 A | 10/1998 | Kreft et al. |
| 5,939,455 A | 8/1999 | Rephaeli |
| 5,955,504 A | 9/1999 | Wechter et al. |
| 5,968,974 A | 10/1999 | Kargman et al. |
| 5,981,592 A | 11/1999 | Wechter et al. |
| 6,066,741 A | 5/2000 | Vigano' et al. |
| 6,110,955 A | 8/2000 | Nudelman et al. |
| 6,160,018 A | 12/2000 | Wechter et al. |
| 6,300,313 B1 | 10/2001 | Engel et al. |
| 6,545,034 B1 | 4/2003 | Carson et al. |
| 6,552,055 B1 | 4/2003 | Spiegelman et al. |
| 7,105,560 B1 | 9/2006 | Carson et al. |
| 7,105,561 B2 | 9/2006 | Carson et al. |
| 7,129,262 B2 | 10/2006 | Carson et al. |
| 7,151,100 B1 | 12/2006 | Carson et al. |
| 7,189,752 B2 | 3/2007 | Carson et al. |
| 7,211,599 B2 | 5/2007 | Carson et al. |
| 2002/0042375 A1 | 4/2002 | Heimbrook et al. |
| 2003/0004142 A1 | 1/2003 | Prior et al. |
| 2003/0004143 A1 | 1/2003 | Prior et al. |
| 2005/0239752 A1 | 10/2005 | Carson et al. |
| 2007/0111950 A1 | 5/2007 | Carson et al. |

FOREIGN PATENT DOCUMENTS

| | | |
|---|---|---|
| AU | 1999520989 | 2/2000 |
| CA | 1299577 | 4/1992 |
| DE | 2226340 | 3/1973 |
| EP | 0289262 | 11/1986 |
| EP | 0289262 A3 | 11/1988 |

(Continued)

OTHER PUBLICATIONS

*1991 New Drugs*, (Sep. 1991),42-60.
*Drug Facts and Comparisons, 1995 Edition*, Wolters Kluwer Co.,(1995),2775-2789.
*The Merck Index, Thirteenth Edition*, Budavari, S., et al., (eds.), Merck & Co., Inc., Rahway, N.J., "Etodolac, Entry No. 3905 ",(1990),p. 685.
In: *Remington's Pharmaceutical Sciences, Eighteenth Edition*, Gennaro, A.R., (ed.), Mack Publishing Company, Easton, PA,(1990),pp. 1115-1122.
"1991 New Drugs", *US Pharmacist*, 61, Pages not cited are advertisements,(Sep. 1991),35-40, 42, 44,46, 48-50, 52, 57-58, 60, 62, 64.

(Continued)

*Primary Examiner*—Rebecca Anderson
*Assistant Examiner*—Michael P. Barker
(74) *Attorney, Agent, or Firm*—Schwegman, Lundberg & Woessner, P.A.

(57) ABSTRACT

The present invention provides novel indole derivatives useful to inhibit cancer or sensitize cancer cells to chemotherapeutic agents, radiation or other anti-cancer treatments.

5 Claims, 16 Drawing Sheets

FOREIGN PATENT DOCUMENTS

| GB | 1436893 | 5/1976 |
|---|---|---|
| WO | WO-96/28148 | 9/1996 |
| WO | WO-9628148 A2 | 9/1996 |
| WO | WO-9748391 A3 | 12/1997 |
| WO | WO-98/09603 | 3/1998 |
| WO | WO-9809603 A2 | 3/1998 |
| WO | WO-98/18490 | 5/1998 |
| WO | WO-98/40078 A1 | 9/1998 |
| WO | WO-00/02555 | 1/2000 |
| WO | WO-00/13410 | 3/2000 |
| WO | WO-0106990 A2 | 2/2001 |
| WO | WO01/014448 | 3/2001 |
| WO | WO-02/02125 A1 | 1/2002 |
| WO | WO-0212188 A2 | 2/2002 |

OTHER PUBLICATIONS

"International Search Report for PCT/US2004/032185", 2005.
Abramson, S. B., et al., "The Mechanisms of Action of Nonsteroidal Antiinflammatory Drugs", *Arthritis & Rheumatism*, 32 (1), (Jan. 1989),1-9.
Alexanian, R. , et al., "The Treatment of Multiple Myeloma", *The New England Journal of Medicine*, 330 (7), (Feb. 17, 1994),484-489.
Barlogie, B , "Prognostic Factors with High-Dose Melphalan for Refractory Multiple Myeloma."*Blood*, 72(6), (Dec. 1988),2015-2019.
Bataille, R , et al., "Multiple Myeloma", *New England Journal of Medicine*, 336, (1997),1657-1664.
Becker-Scharfenkamp, U. , et al., "Evaluation of the Stereoselective Metabolism of the Chiral Analgesic Drug Etodolac by High-Performance Liquid Chromatography", *Journal of Chromatography*, 621 (2), (Nov. 24, 1993),pp. 199-207.
Bellosillo, Beatriz , et al., "Aspirin and Salicylate Induce Apoptosis and Activation of Caspases in B-Cell Chronic Lymphocytic Leukemia Cells", *Blood*, 92 (4), (Aug. 15, 1998),1406-1414.
Berendes, U. , et al., "Simultaneous Determination of the Phase II Metabolites of the Non Steriodal Anti-Inflammatory Drug Etodolac in Human Urine", *Enantiomer*, 1, Abstract Only, Chemical Abstracts, Abstract No. 126:207064q,(1996),415-422.
Berendes, U. , et al., "Simultaneous Determination of the Phase II Metabolites of the Non Steroidal Anti-Inflammatory Drug Etodolac", *Chemical Abstracts*, 126, Abstract No. 207064,(Apr. 21, 1997),p. 9.
Berkow, et al., *The Merck Manual of Medical Information*, Merck Research Laboratories,(1997),p. 765-66 and 779-80.
Brenna, E. , et al., *Tetrahedron*, vol. 53 (52), (1997),17769-17780.
Brenna, Elisabetta , et al., "New Enzymatic and Chemical Approaches to Enantiopur Etodolac", *Tetrahedron*, vol. 53, No. 52, (1997),17769-17780.
Brenna, E. , et al., "New Enzymatic and Chemical Approaches to Enantiopure Etodolac", *Tetrahedron*, 53, (1997),17769-17780.
Brocks, D. R., et al., "Etodolac Clinical Pharmacokinetics", *Clinical Pharmacokinetics*, 26(4), (1994),pp. 259-274.
Carson, D. A., et al., "Oral Antilymphocyte Activity and Induction of Apoptosis by 2-chloro-2'-arabino-fluoro-2'-deoxyadenosine", *Proceedings of the National Academy of Sciences USA*, 89 (7), (Apr. 1, 1992),2970-2974.
Chinetti, G. , et al., "Activation of Proliferator-activated Receptors alpha and Y Induces Apoptosis of Human Monocyte-derived Macrophages", *Journal of Biological Chemistry*, 273 (40), (Oct. 2, 1998),25573-25580.
Cunningham, D , et al., "High-dose Melphalan for Multiple Myeloma: Long-term Follow-up Data", *Journal of Clinical Oncology*, 12, (1994),764-768.
Demerson, C. A., et al., "Etodolic Acid and Related Compounds. Chemistry and Antiinflammatory Actions of Some Potent Di- and Trisubstituted 1,3,4,9-Tetrahydropyrano[3,4-b]indole-1-acetic Acids", *Journal of Medicinal Chemistry*, 19 (3), (1976),pp. 391-395.

Demerson, C. A., et al., "Resolution of Etodolac and Antiinflammatory and Prostaglandin Synthetase Inhibiting Properties of the Enantiomers", *J. Med. Chem.*, 26 (12), (Dec. 1983),pp. 1778-1780.
Drachenberg, D. E., "Treatment of Prostate Cancer: Watchful Waiting, Radical Prostatectomy, and Cryoablation", *Seminars in Surgical Oncology*, 18 (1), (Jan./Feb. 2000),pp. 37-44.
Duffy, C. P., et al., "Enhancement of Chemotherapeutic Drug Toxicity to Human Tumour Cells In Vitro by a Subset of Non-Steroidal Anti-Inflammatory Drugs (NSAIDs)", *European Journal of Cancer*, 34 (8), (Jul. 1998),pp. 1250-1259.
Hahnfeld, L. E., et al., "Prostate Cancer", *The Medical Clinics of North America—The Aging Male Patient*, 83 (5), (Sep. 1999),pp. 1231-1245.
Harousseau, J.L., et al., "Double-Intensive Therapy in High-Risk Multiple Myeloma", *Blood*, 79 (11), (Jun. 1, 1992),pp. 2827-2833.
Heath, Clark W., "Nonsteroidal Antiinflammatory Drugs and Human Cancer", *American Cancer Society*, vol. 74, No. 10, (Nov. 15, 1994),2885-2886.
Kamijo, T. , et al., "Induction of apoptosis by cyclooxygenase-2 inhibitors in prostate cancer cell lines", *International Journal of Urology*, 8(7), (2001),S35-S39.
Kolluri, S. K., et al., "The R-Enantiomer of the Nonsteroidal Antiinflammatory Drug Etodolac Binds Retinoid X Receptor and Induces Tumor-Selective Apoptosis", *Proc. Natl. Acad. Sci. USA*, 102(7), (2005),2525-2530.
Krajewski, S. , et al., "Detection of Multiple Antigens on Western Blots", *Analytical Biochemistry*, 236 (2), Article No. 0160,(May 1996),pp. 221-228.
Landis, S. H., et al., "Cancer Statistics, 1998", *CA Cancer J. Clin.*, 48 (1), (1998),pp. 6-29.
Lee, D. H., "Proteasome Inhibitors: Valuable New Tools For Cell Biologists", *Trends in Cell Biology*, 8, (Oct. 1998),pp. 397-403.
Lehmann, J. M., et al., "Peroxisome Proliferator-activated Receptors alpha and Y Are Activated by Indomethacin and Other Nonsteroidal Anti-inflammatory Drugs", *Journal of Biological Chemistry*, 272 (6), (Feb. 7, 1997),3406-3410.
Leman, Eddy S., et al., "Characterization of the Nuclear Matrix Proteins in a Transgenic Mouse Model for Prostate Cancer", *Journal of Cellular Biochemistry*, 86, (2002),203-212.
Leoni, L. M., et al., "Induction of an Apoptotic Program in Cell-Free Extracts by 2-Chloro-2'-deoxyadenosine 5'-triphosphate and Cytochrome C", *PNAS, USA*, 95 (16), (Aug. 4, 1998),pp. 9567-9571.
Lochmuller, C. H., et al., "Chromatographic Resolution of Enantiomers—Selective Review", *Journal of Chromatography*, 113 (3), (Oct. 22, 1975),283-302.
Martel, R. R., et al., "Anti-inflammatory and Analgesic Properties of Etodolic Acid in Rats", *Canadian Journal of Physiology and Pharmacology*, 54 (3), (Jun. 1976),pp. 245-248.
McCracken, John D., "Antiproliferative Effects of the Enantiomers of Flurbiprofen", *Journal of Clinical Pharmacology*, (1996),540-545.
Mooney, P. T., et al., "Cell Pathways' Exisulind 'Aptosyn' Demonstrates Potential to Delay Hormone Therapy in Post-Prostatectomy Men at Risk of Prostate Cancer Recurrence", http://biz.yahoo.com/bw/000501/qa_cell_pa_1.html, (May 2000),3 p.
Mycek, M. J., et al., "Anticancer Drugs", *Lippincott's Illustrated Reviews: Pharmacology, Second Edition*, (1997),p. 373, 387-395.
Nardella, Francis A., et al., "Enhanced Clearance of Leukemic Lymphocytes in B Cell Chronic Lymphocytic Leukemia (CLL) with Etodolac", *Arthritis & Rheumatism*, 42 (9) Supplement, Abstract No. 41, (Sep. 1999),p. S56.
Piazza, Gary A., "Apoptois Primarily Accounts for the Growth-Inhibitory Properties of Sulindac Metabolites and Involves a Mechanism That is Independent of Cyclooxygebase Inhibition, Cell Cycles Arrest, and p53 Induction", *Cancer Research*, vol. 57, (Jun. 15, 1997),2452-2459.
Ricote, M. , et al., "The Peroxisome Proliferator-Activated Receptor-Y is a Negative Regulator of Macrophage Activation", *Nature*, 391 , (Jan. 1, 1998),pp. 79-82.
Riedel, D. A., et al., "The Epidemiology of Multiple Myeloma", *Hematology/Oncology Clinics of North America, Multiple Myeloma*, 6 (2), (Apr. 1992),pp. 225-247.

Riley, et al., "New Drugs: a six month review", *US Pharamacist*, vol. 16, (Sep. 1991),35-64.

Royall, J. A., et al., "Evaluation of 2',7'-Dichlorofluorescin and Dihydrorhodamine 123 as Fluorescent Probes for Intracellular H2O2 in Cultured Endothelial Cells", *Archives of Biochemistry and Biophysics*, 302 (2), (May 1, 1993),pp. 348-355.

Shiff, S. J., et al., "Nonsteroidal Antiinflammatory Drugs Inhibit the Proliferation of Colon Adenocarcinoma Cells: Effects on Cell Cycle and Apoptosis", *Experimental Cell Research*, 222, Article No. 0023,(1996),pp. 179-188.

Tang, D. G., et al., "Target to Apoptosis: A Hopeful Weapon for Prostate Cancer", *The Prostate*, (1997),pp. 284-293.

Thun, Michael J., "Aspirin, NSAIDs, and digestive tract cancers", *Cancer and Metastasis Reviews 13*, Kluwer Academic Publishers., (1994),269-277.

Van Breemen, R. B., et al., "Characterization of Oxygen-Linked Glucuronides by Laser Desorption Mass Spectrometry", *Biomed. Mass Spectrom.*, 11, Abstract Only, Chemical Abstracts, Abstract No. 101:106777c,(1984),278-283.

Venuti, M. C., et al., "Synthesis and Biological Evaluation of omega-(N,N,N-trialkylammonium)alkyl Esters and Thioesters of Carboxylic Acid Nonsteroidal Antiinflammatory Agents", *Pharm. Res.*, 6, Abstract Only, Chemical Abstracts, Abstract No. 112:111681y,(1989),867-873.

Venuti, M. C., et al., "Synthesis and Biological Evaluation of omega-(N,N,N-trialkylammonium)alkyl Esters and Thioesters of Carboxylic Acid Nonsteroidal Antiinflammatory Agents", *Chemical Abstracts*, 112,, Abstract No. 111681,(Mar. 26, 1990),p. 34.

Wang, X., et al., "Antipoptotic Action of 1,25-Dihydroxyvitamin D3 Is Associated with Increased Mitochondrial MCL-1 and RAF-1 Proteins and Reduced Release of Cytochrome c", *Experimental Cell Research*, 235 (1), Article No. EX973667,(1997),pp. 210-217.

Wechter, W. J., et al., "E-7869 (R-Flurbiprofen) Inhibits Progression of Prostate Cancer in the TRAMP Mouse", *Cancer Research*, 60, (Apr. 15, 2000),pp. 2203-2208.

Wechter, William J., "R-Flurbiprofen (E-7869), a chemopreventive and treatment of cancer", *Inflammopharmacology*, vol. 8, No. 2, (2000),189-206.

Wechter, William J., "R-Flurbiprofen Chemoprevention and Treatment of Intestinal Adenomas in the APC min/+ Mouse Model: Implications for Prophylaxis and Trearment of Colon Cancer", *Cancer Research*, vol. 57, No. 19, (Oct. 1, 1997),4316-4324.

Wechter, William J., "Rac-Flurbiprofen Is More Ulcerogenic Than Its (S)-Enantiomer", *Chirality*, vol. 5, No. 7, (1993),492-494.

Weiss, H. A., et al., "Aspirin, Non-Steroidal Anti-Inflammatory Drugs and Protection from Colorectal Cancer: a Review of the Epidemiological Evidence", *Scandinavian Journal of Gastroenterology*, 31 (Suppl. 220), (1996),pp. 137-141.

Wilen, S. H., et al., "Strategies In Optical Resolutions", *Tetrahedron*, 33 (21), Tetrahedron Report No. 38,(1977),pp. 2725-2736.

Yasui, H., et al., "SDX-101, the R-enantiomer of etodolac, induces cytotoxicity, overcomes drug resistance, and enchances the activity of dexamethasone in multiple myeloma", *Blood, Neoplasia*, 106(2), (Jul. 15, 2005),706.

"U.S. Appl. No. 09/634,207, Response filed Mar. 17, 2003 to Final Office Action mailed Nov. 15, 2002", 7 pgs.

"U.S. Appl. No. 09/360,020 Final Office Action mailed Nov. 30, 2001", 5 pgs.

"U.S. Appl. No. 09/360,020, Non-Final Office Action mailed Mar. 16, 2001", 11 pgs.

"U.S. Appl. No. 09/360,020, Non-Final Office Action mailed Apr. 12, 2002", 3 pgs.

"U.S. Appl. No. 09/360,020, Notice of Allowance mailed Nov. 8, 2002", 9 pgs.

"U.S. Appl. No. 09/360,020, Response filed Mar. 7, 2002 to Final Office Action Nov. 30, 2001", 6 pgs.

"U.S. Appl. No. 09/360,020, Response filed Sep. 14, 2001 to Non-Final Office Action mailed Mar. 16, 2001", 7 pgs.

"U.S. Appl. No. 09/360,020, Supplemental Amendment filed Apr. 3, 2002", 3 pgs.

"U.S. Appl. No. 09/360,020, Supplemental Amendment filed Oct. 24, 2002", 2 pgs.

"U.S. Appl. No. 09/589,476, Final Office Action mailed Jul. 25, 2002", 5 pgs.

"U.S. Appl. No. 09/589,476, Final Office Action mailed Dec. 29, 2005", 7 pgs.

"U.S. Appl. No. 09/589,476, Non-Final Office Action mailed Jan. 5, 2004", 6 pgs.

"U.S. Appl. No. 09/589,476, Non-Final Office Action mailed Mar. 11, 2002", 4 pgs.

"U.S. Appl. No. 09/589,476, Non-Final Office Action mailed May 4, 2005", 8 pgs.

"U.S. Appl. No. 09/589,476, Non-Final Office Action mailed May 23, 2003", 5 pgs.

"U.S. Appl. No. 09/589,476, Notice of Allowance mailed Apr. 17, 2006", 9 pgs.

"U.S. Appl. No. 09/589,476, Response filed Jan. 27, 2003 to Final Office action Jul. 25, 2002", 1 pgs.

"U.S. Appl. No. 09/589,476, Response filed Mar. 24, 2006 to Final Office Action mailed Dec. 29, 2005", 9 pgs.

"U.S. Appl. No. 09/589,476, Response filed Apr. 29, 2002 to Non-Final Office Action mailed Mar. 11, 2002", 4 pgs.

"U.S. Appl. No. 09/589,476, Response filed Jun. 7, 2004 to Non-Final Office Action mailed Jan. 5, 2004", 10 pgs.

"U.S. Appl. No. 09/589,476, Response filed Sep. 6, 2005 to Non-Final Office Action mailed May 4, 2005", 10 pgs.

"U.S. Appl. No. 09/589,476, Response filed Aug. 23, 2003 to Non-Final Office Action mailed May 23, 2003", 7 pgs.

"U.S. Appl. No. 09/634,207, Final Office Action mailed Nov. 15, 2002", 5 pgs.

"U.S. Appl. No. 09/634,207, Non-Final Office Action mailed Jan. 14, 2004", 7 pgs.

"U.S. Appl. No. 09/634,207, Non-Final Office Action mailed May 2, 2002", 7 pgs.

"U.S. Appl. No. 09/634,207, Notice of Allowance mailed Jan. 11, 2005", 6 pgs.

"U.S. Appl. No. 09/634,207, Notice of Allowance mailed May 20, 2003", 8 pgs.

"U.S. Appl. No. 09/634,207, Notice of Allowance mailed Jun. 27, 2006", 4 pgs.

"U.S. Appl. No. 09/634,207, Notice of Allowance mailed Sep. 14, 2004", 6 pgs.

"U.S. Appl. No. 09/634,207, Preliminary Amendment filed Feb. 28, 2005", 6 pgs.

"U.S. Appl. No. 09/634,207, Preliminary Amendment filed Aug. 19, 2003", 8 pgs.

"U.S. Appl. No. 09/634,207, Response filed Jul. 14, 2004 to Non-Final Office Action mailed Jan. 14, 2004", 8 pgs.

"U.S. Appl. No. 09/634,207, Response filed Sep. 3, 2002 to Non-Final Office Action May 2, 2002", 10 pgs.

"U.S. Appl. No. 09/634,207, Supplemental Amendment filed Apr. 15, 2003", 7 pgs.

"U.S. Appl. No. 10/236,221, Final Office Action mailed Feb. 2, 2005", 7 pgs.

"U.S. Appl. No. 10/236,221, Non-Final Office Action mailed Aug. 8, 2003", 5 pgs.

"U.S. Appl. No. 10/236,221, Non-Final Office Action mailed Aug. 24, 2005", 11 pgs.

"U.S. Appl. No. 10/236,221, Response filed Jan. 8, 2004 to Non-Final Office Action mailed Aug. 8, 2003", 10 pgs.

"U.S. Appl. No. 10/236,221, Response filed Jan. 24, 2006 to Non-Final Office Action mailed Aug. 24, 2005", 8 pgs.

"U.S. Appl. No. 10/236,221, Response filed Jun. 2, 2005 to Final Office Action mailed Feb. 2, 2005", 9 pgs.

"U.S. Appl. No. 10/236,221, Notice of Allowance Recieved Apr. 19, 2006", 12 pgs.

"U.S. Appl. No. 10/236,221, Preliminary Amendment filed Dec. 16, 2002.", 1 pg.

"U.S. Appl. No. 10/667,208, Non-Final Office Action mailed Jun. 16, 2004", 5 pgs.

"U.S. Appl. No. 10/667,208, Notice of Allowance mailed Jun. 14, 2006", 4 pgs.

"U.S. Appl. No. 10/667,208, Notice of Allowance mailed Sep. 7, 2005", 5 pgs.

"U.S. Appl. No. 10/667,208, Notice of Allowance mailed Dec. 22, 2004", 4 pgs.

"U.S. Appl. No. 10/667,208, Response filed Aug. 24, 2006 to Notice of Allowance mailed Jun. 14, 2006", 4 pgs.

"U.S. Appl. No. 10/667,208, Response filed Nov. 16, 2004 to Non-Final Office Action mailed Jun. 16, 2004", 5 pgs.

"U.S. Appl. No. 10/753,665, Final Office Action mailed Sep. 9, 2005", 5 pgs.

"U.S. Appl. No. 10/753,665, Non-Final Office Action mailed Mar. 22, 2006", 11 pgs.

"U.S. Appl. No. 10/753,665, Non-Final Office Action mailed Dec. 30, 2004", 7 pgs.

"U.S. Appl. No. 10/753,665, Notice of Allowance mailed Oct. 19, 2006", 7 pgs.

"U.S. Appl. No. 10/753,665, Response filed Feb. 9, 2006 to Final Office Action mailed Sep. 9, 2005", 7 pgs.

"U.S. Appl. No. 10/753,665, Response filed Jun. 15, 2005 to Non-Final Office Action mailed Dec. 30, 2004", 9 pgs.

"U.S. Appl. No. 10/753,665, Response filed Jul. 24, 2006 to Non-Final Office Action mailed Mar. 22, 2006", 8 pgs.

"U.S. Appl. No. 11/013,955, Non-Final Office Action mailed Dec. 16, 2005", 10 pgs.

"U.S. Appl. No. 11/013,955, Notice of Allowance mailed May 15, 2006", 6 pgs.

"U.S. Appl. No. 11/013,955, Preliminary Amendment Jul. 6, 2005", 3 pgs.

"U.S. Appl. No. 11/013,955, Response filed Apr. 18, 2006 to Non-Final Office Action mailed Dec. 16, 2005", 10 pgs.

"U.S. Appl. No. 11/612,414, Preliminary Amendment filed Dec. 18, 2006", 5 pgs.

INDOLE COMPOUNDS USEFUL FOR THE TREATMENT OF CANCER

CROSS-REFERENCE TO RELATED APPLICATIONS

This application is a divisional of U.S. patent application Ser. No. 11/013,955 filed Dec. 16, 2004, issued as U.S. Pat. No. 7,129,262, on Oct. 31, 2006, which is a continuation-in-part of U.S. patent application Ser. No. 09/634,207 filed Aug. 9, 2000, issued as U.S. Pat. No. 7,151,100, on Dec. 19, 2006, which is a continuation-in-part of U.S. patent application Ser. No. 09/360,020 filed Jul. 23, 1999, issued as U.S. Pat. No. 6,545,034, on Apr. 8, 2003; which are incorporated by reference herein.

The invention was made with Government support under Grant No. 5ROI GM23200-24 awarded by the National Institute of Health. The Government has certain rights in the invention.

BACKGROUND OF THE INVENTION

Prostate cancer is the second leading cause of cancer death among males in the United States. In 1998, an estimated 185,000 men were diagnosed with prostate cancer, and more than 39,000 men died of the disease. See, S. H. Landis et al., Cancer Statistics, *CA Cancer J. Clin.*, 48, 6 (1998). Although survival rates are good for prostate cancer that is diagnosed early, the treatments for advanced disease are limited to hormone ablation techniques and palliative care. Hormone ablation techniques (orchiectomy and anti-androgen treatments) generally allow only temporary remission of the disease. It usually recurs within 1-3 years of treatment, with the recurrent tumors no longer requiring androgens for growth and survival. D. G. Tang et al., *Prostate*, 32, 284 (1997). Therapy with conventional chemotherapeutic agents, such as progesterone, estramustine and vinblastine, has also not been demonstrated to be effective to halt progression of the disease.

The number of nonsteroidal anti-inflammatory drugs (NSAIDs) has increased to the point where they warrant separate classification. In addition to aspirin, the NSAIDs available in the U.S. include meclofenamate sodium, oxyphenbutazone, phenylbutazone, indomethacin, piroxicam, sulindac and tolmetin for the treatment of arthritis; mefenamic acid and zomepirac for analgesia; and ibuprofen, fenoprofen and naproxen for both analgesia and arthritis. Ibuprofen, mefenamic acid and naproxen are used also for the management of dysmenorrhea.

The clinical usefulness of NSAIDs is restricted by a number of adverse effects. Phenylbutazone has been implicated in hepatic necrosis and granulomatous hepatitis; and sulindac, indomethacin, ibuprofen and naproxen with hepatitis and cholestatic hepatitis. Transient increases in serum aminotransferases, especially alanine aminotransferase, have been reported. All of these drugs, including aspirin, inhibit cyclooxygenase, that in turn inhibits synthesis of prostaglandins, which help regulate glomerular filtration and renal sodium and water excretion. Thus, the NSAIDs can cause fluid retention and decrease sodium excretion, followed by hyperkalemia, oliguria and anuria. Moreover, all of these drugs can cause peptic ulceration. See, *Remington's Pharmaceutical Sciences*, Mack Pub. Co., Easton, Pa. (18th ed., 1990) at pages 1115-1122.

There is a large amount of literature on the effect of NSAIDs on cancer, particularly colon cancer. For example, see H. A. Weiss et al., *Scand J. Gastroent.*, 31, 137 (1996) (suppl. 220) and Shiff et al., *Exp. Cell Res.*, 222, 179 (1996). More recently, B. Bellosillo et al., *Blood*, 92, 1406 (1998) reported that aspirin and salicylate reduced the viability of B-cell CLL cells in vitro, but that indomethacin, ketoralac and NS-398, did not.

C. P. Duffy et al., *Eur. J. Cancer*, 34, 1250 (1998), reported that the cytotoxicity of certain chemotherapeutic drugs was enhanced when they were combined with certain non-steroidal anti-inflammatory agents. The effects observed against human lung cancer cells and human leukemia cells were highly specific and not predictable; i.e., some combinations of NSAID and agent were effective and some were not. The only conclusion drawn was that the effect was not due to the cyclooxygenase inhibitory activity of the NSAID.

The Duffy group filed a PCT application (WO98/18490) on Oct. 24, 1997, directed to a combination of a "substrate for MRP", which can be an anti-cancer drug, and a NSAID that increases the potency of the anti-cancer drug. NSAIDs recited by the claims are acemetacin, indomethacin, sulindac, sulindac sulfide, sulindac sulfone, tolmetin and zomepirac. Naproxen and piroxicam were reported to be inactive.

Recently, W. J. Wechter et al., *Cancer Res.*, 60, 2203 (2000) reported that the NSAID, R-flurbiprofen, inhibited progression of prostate cancer in the TRAMP mouse, a prostate cancer model. The Wechter group filed a PCT application (WO98/09603) on Sep. 8, 1997, disclosing that prostate cancer can be treated with R-NSAIDs, including R(−)-etodolac and R-flurbiprofen. In contrast to R(−)-etodolac, the R-enantiomer of flurbiprofen and other (R)-2-aryl propionate NSAIDs are converted in the body to the anti-inflammatory S-enantiomers, and hence are pro-drugs of the NSAIDs, while R(−)-etodolac is not per se an NSAID. Therefore, a continuing need exists for effective methods to employ these preliminary findings to develop new compounds to treat neoplastic disease, including prostate cancer and other cancers.

SUMMARY OF THE INVENTION

The present invention provides indole compounds of formula (I):

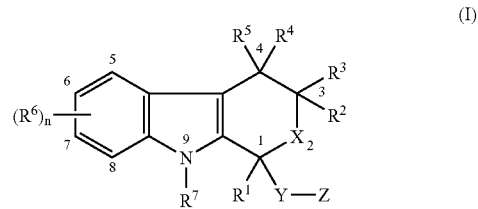

wherein $R^1$ is lower alkyl, lower alkenyl, (hydroxy)lower alkyl, lower alkynyl, phenyl, benzyl or 2-thienyl, $R^2$, $R^3$, $R^4$ and $R^5$ are the same or different and are each hydrogen or lower alkyl; each $R^6$ is individually hydrogen, lower alkyl, hydroxy, (hydroxy)lower alkyl, lower alkoxy, benzyloxy, lower alkanoyloxy, nitro or halo, n is 1-3, $R^7$ is hydrogen, lower alkyl or lower alkenyl, X is oxy and thio, Y is carbonyl, $(CH_2)_{1-3}$, $(CH_2)_{1-3}C(O)$, or $(CH_2)_{1-3}SO_2$ and Z is (ω-(4-pyridyl)($C_2$-$C_4$ alkoxy), (ω-(($R^8$)($R^9$)amino)($C_2$-$C_4$ alkoxy), wherein $R^8$ and $R^9$ are each H, ($C_1$-$C_3$)alkyl or together with N are a 5- or 6-membered heterocyclic ring comprising 1-3 N($R^8$), S or nonperoxide O; an amino acid ester of (ω-(HO)($C_2$-$C_4$))alkoxy, $N(R^8)CH(R^8)CO_2H$, 1N-D-glucuronyloxy; Y-Z is $(CH_2)_{1-3}R^8$ wherein $R^8$ is OH, (C$_2$-C$_4$)acyloxy, SO$_3$H, PO$_4$H$_2$, N(NO)(OH), SO$_2$NH$_2$, PO(OH)NH$_2$, or tetrazolyl; or a pharmaceutically acceptable salt thereof.

The present invention also provides a therapeutic method to inhibit the growth of cancer cells and/or to sensitize cancer cells to inhibition by a chemotherapeutic agent. The method comprises contacting cancer cells with an effective amount of the compound of formula (I), preferably in combination with a pharmaceutically acceptable carrier. The present compounds can be used to treat a mammal afflicted with cancer, such as a human cancer patient, and are preferably administered in conjunction with a chemotherapeutic agent, such as an alkylating agent or an anti-androgen, radiation and/or other anti-cancer therapy.

The present compounds are effective against hematopoietic cancers, such as leukemias and cancers of the bone marrow, including chronic lymphocytic leukemia (CLL) and multiple myeloma (MM). The present compounds were unexpectedly found to be effective against cancer cells that express high levels of the nuclear hormone receptor, peroxisome proliferator activated receptor-γ, (PPAR-γ), and/or high levels of the anti-apoptotic proteins, Mcl-1 and/or Bag-1. Such cancer cells include at least some types of prostate cancer cells.

Activated PPAR-γ binds co-activator protein (CBP), a co-activator of the androgen receptor known to be overexpressed in hormone-resistant prostate cancer. Thus, compounds of formula (I) that activate PPAR-γ production can reduce the level of expression of the androgen receptor known to be over-expressed in hormone-resistant prostate cancer. Therefore, the present compounds can enhance the efficacy of conventional anti-androgen therapy, and can act to inhibit the spread of prostate cancer. The cancer cells would be susceptible to inhibition by a compound of formula (I) when the level of PPAR-γ in the cells is sufficiently high, i.e., the level is at least about fifty percent higher than the level of PPAR-γ in normal prostate cells, as measured by a standard technique such as, for example, immunoprecipitation or imunoblotting.

The present invention is based on the discovery by the inventors that racemic etodolac inhibits the viability of purified CLL or MM cells at concentrations that do not inhibit the viability of normal peripheral blood lymphocytes (PBLs). It was then unexpectedly found that the R(−) enantiomer of etodolac is as toxic to CLL cells as is the S(+) enantiomer. It was then found that etodolac synergistically interacted with fludarabine and 2-chloroadenosine to kill CLL cells at concentration at which the chemotherapeutic agents alone were inactive. Finally, it was found that both R(−)- and S(+)-etodolac inhibited a number of prostate cancer cell lines. Again the R(−) enantiomer was at least as effective as the S(+)-"anti-inflammatory" enantiomer. This was unexpected since the R(−) enantiomer of etodolac does not possess significant anti-inflammatory activity and is not converted to the S(+) enantiomer to a significant extent in vivo. As noted above, the R-enantiomers of other R-2-arylpropionate NSAIDs are converted to the "active" anti-inflammatory S-enantiomers in vivo, and so function as pro-drugs for the NSAID.

The extent of inhibition was markedly related to the level of expression of PPAR-γ by the cell line. Cell lines with an elevated level of PPAR-γ expression were inhibited much more effectively than cell lines expressing relatively low levels of PPAR-γ, as disclosed in the working examples.

A compound of formula (I) is preferred for practice of the present therapeutic method that does not exhibit undesirable bioactivities due to inhibition of cyclooxygenase (COX) that are exhibited by some NSAIDs. However, the preferred compounds of formula (I) would not be considered NSAIDs by the art, as they would not exhibit significant anti-inflammatory activity.

Thus, the present invention also provides a method for determining whether or not a particular cancer patient, such as a prostate cancer patient, is amenable to treatment by a compound of formula (I), comprising isolating cancer cells and evaluating in vitro the relative level of PPAR-γ and/or Mcl-1 and/or Bag-1 relative to the level in a cancer cell line, such as prostate cancer cell line, known to be susceptible to treatment by a compound of formula (I).

The present invention also provides a method to determine the ability of a test agent to inhibit cancer cells, such as prostate cancer cells, comprising contacting a population of cancer cells, as from a prostate cancer cell line, with said agent and determining whether the agent increases expression of PPAR-γ, or decreases the expression of Mcl-1 and/or Bag-1 (or does both). The present invention also provides a general multilevel screening method to evaluate etodolac analogs, other NSAIDs or other agents for their ability to inhibit cancer, preferably etodolac-sensitive cancers, such as prostate cancer, CLL and MM. Agents that exhibit a positive activity, preferably at least equal to that of R(−)-etodolac, or do not exhibit a negative activity, e.g., are no more active than R(−)-etodolac, are passed to the next screen.

Test agents are first evaluated for their ability to competitively inhibit the binding of etodolac, e.g., radiolabeled R(−)-etodolac to its receptor(s) on etodolac-sensitive cancer cells such as CLL cells. Agents that can compete effectively with R(−)-etodolac for etodolac binding site(s) on the cells are then evaluated in an assay to determine if they can increase Ca$^{+2}$ uptake in cancer cells, such as CLL cells, preferably as effectively as R(−)-etodolac. Agents that can induce intracellular Ca$^{+2}$ uptake are screened to determine if they can induce chemokinetic activity (chemokinesis or chemotaxis) in a population of lymphocytes, such as B-CLL lymphocytes, preferably as effectively as R(−)-etodolac. Agents that are positive in this screen are then evaluated to determine if they can induce apoptosis or pro-apoptotic factors, such as increased caspase activity in cancer cells, such as CLL cells and other cancer cells known to be etodolac sensitive, at least as effectively as R(−)-etodolac.

Agents that test positive in this screen are evaluated for their ability to deplete lymphocytes in mice, and those that are no more active than R(−)-etodolac are then evaluated in animal models of cancer to see if they can inhibit the induction of, or spread of cancer.

As used herein with respect to cancer or cancer cells, the term "inhibition" or "inhibit" includes both the reduction in cellular proliferation, blockage of cellular proliferation, or killing some or all of said cells. Thus, the term can be used in both the context of a prophylactic treatment to prevent development of cancer or as a treatment that will block, or slow the spread of established cancer. Whether or not the level of expression of a marker of susceptibility to etodolac treatment is sufficiently elevated to continue treatment with etodolac or an analog thereof is determined by comparison between the relative levels of expression of said marker in resistant and susceptible cancer cell lines, as disclosed hereinbelow.

DETAILED DESCRIPTION OF THE INVENTION

Figure 1:
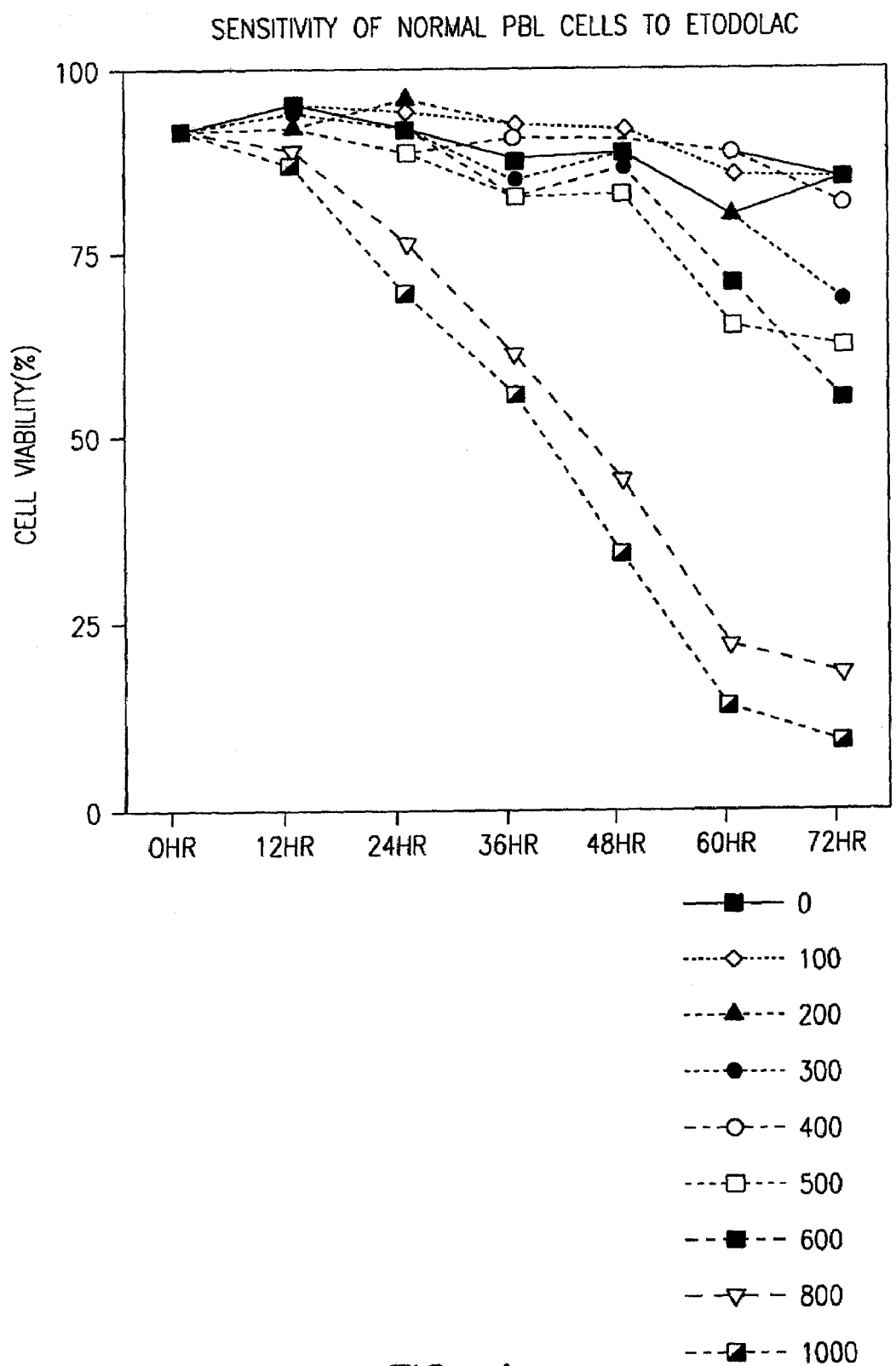
FIG. 1 is a graph depicting the sensitivity of normal peripheral blood lymphocytes (PBL) to racemic etodolac.

Indole compounds of the present inventions include compounds of formula (I):

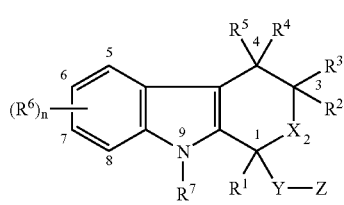

(I)

wherein $R^1$ is lower alkyl, lower alkenyl, (hydroxy)lower alkyl, lower alkynyl, phenyl, benzyl or 2-thienyl; $R^2$, $R^3$, $R^4$ and $R^5$ are the same or different and are each hydrogen or lower alkyl; each $R^6$ is individually hydrogen, lower alkyl, hydroxy, (hydroxy)lower alkyl, lower alkoxy, benzyloxy, lower alkanoyloxy, nitro or halo, n is 1-3; $R^7$ is hydrogen, lower alkyl or lower alkenyl; X is oxy or thio; Y is $(CH_2)_{1-3}$, or $(CH_2)_{1-3}SO_2$, and Z is (ω-(4-pyridyl)($C_2$-$C_4$alkoxy), (ω-(($R^8$)($R^9$)amino)($C_2$-$C_4$ alkoxy), an amino acid ester of (ω-(HO)($C_2$-$C_4$))alkoxy, $N(R^8)CH(R^8)CO_2H$, 1'-D-glucuronyloxy, or $OCH_2CH_2N(CH_3)_3^+$; wherein $R^8$ and $R^9$ are each H, ($C_1$-$C_3$)alkyl or together with N, are a 5- or 6-membered heterocyclic ring having 1-3 $N(R^8)$, S or nonperoxide O; or Y-Z is $(CH_2)_{1-3}R^{10}$ wherein $R^{10}$ is OH, ($C_2$-$C_4$)acyloxy, $SO_3H$, $PO_4H_2$, N(NO)(OH), $SO_2NH_2$, PO(OH)$NH_2$, provided that when n is 1, $R^6$ is hydrogen, and $R^1$ is methyl, then— Y-Z is not —$CH_2CH_2$—OH, —$CH_2$—OH, —$CH_2CH_2$—OC(O)$CH_3$, or —$CH_2$—OC(O)$CH_3$; or tetrazolyl; provided that when n is 1, $R^6$ is 8-ethyl, and $R^1$ is ethyl, then— Y-Z is not —$CH_2CH_2$—OH, or —$CH_2CH_2$—OC(O)$CH_3$; or a pharmaceutically acceptable salt thereof.

As discussed above, the relatively low water solubility of the R(-) enantiomer of etodolac can reduce its usefulness against cancer when administered orally, or in an aqueous vehicle. Therefore, the present invention also provides novel indole compounds that exhibit enhanced water solubility and/or bioavailability over the free acid or the simple alkyl esters of etodolac. Such analogs include (pyridinyl) lower alkyl esters, (amino)lower alkyl esters, (hydroxy)lower alkyl esters and 1N-D-glucuronate esters of etodolac, e.g., compounds of formula (II) wherein (a) Y is carbonyl and (b) Z is (ω-(4-pyridyl)($C_2$-$C_4$ alkoxy), (ω-(($R^8$)($R^9$)amino)($C_2$-$C_4$ alkoxy), wherein $R^8$ and $R^9$ are each H, ($C_1$-$C_3$)alkyl or together with N are a 5- or 6-membered heterocyclic ring comprising 1-3 $N(R^8)$, S or nonperoxide O; an amino acid ester of (ω-(HO)($C_2$-$C_4$)alkoxy, e.g., the L-valine or L-glycine ester of 2-hydroxyethoxy, 1N-D-glucuronyloxy; and the pharmaceutically acceptable salts thereof, e.g., with organic or inorganic acids. Other analogs of increased water solubility include amino acid amides, where Y is carbonyl and Z is $N(R^8)CH(R^8)CO_2H$, and the pharmaceutically acceptable salts thereof.

Such compounds can be prepared as disclosed in U.S. Pat. No. 3,843,681, U.S. patent application Ser. No. 09/313,048, Ger. Pat. No. 2,226,340 (Amer. Home Products), R. R. Martel et al., Can. J. Pharmacol., 54, 245 (1976); Demerson et al., J. Med. Chem., 19, 391 (1976); PCT application Serial No. US/00/13410 and Rubin (U.S. Pat. No. 4,337,760).

The resolution of racemic compounds of formula (I) can be accomplished using conventional means, such as the formation of a diastereomeric salt with a optically active resolving amine; see, for example, "Stereochemistry of Carbon Compounds," by E. L. Eliel (McGraw Hill, 1962); C. H. Lochmuller et al., J Chromatog., 113, 283 (1975); "Enantiomers, Racemates and Resolutions," by J. Jacques, A. Collet, and S. H. Wilen, (Wiley-Interscience, New York, 1981); and S. H. Wilen, A. Collet, and J. Jacques, Tetrahedron, 33, 2725 (1977). For example, the racemate has been resolved by fractional crystallization of RS-etodolac using optically active 1-phenylethylamine and HPLC has been used to determine racemic etodolac and enantiomeric ratios of etodolac and two hydroxylated metabolites in urine (U. Becker-Scharfenkamp et al., J. Chromatog., 621, 199 (1993)). B. M. Adger et al. (U.S. Pat. No. 5,811,558), disclosed the resolution of etodolac using glutamine and N($C_1$-$C_4$ alkyl)-glutamine salts.

Etodolac itself (1,8-diethyl-1,3,4,9-tetrahydro[3,4-6]indole-1-acetic acid) is a NSAID of the pyranocarboxylic acid class, that was developed in the early 1970s. Its structure is depicted as formula (II), below, wherein (*) denotes the chiral center. See also, The Merck Index, (11th ed.), at page 608.

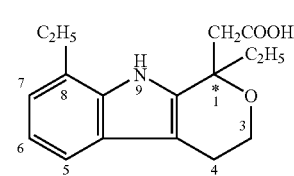

(II)

The pharmacokinetics of etodolac have been extensively reviewed by D. R. Brocks et al., *Clin. Pharmacokinet.*, 26, 259 (1994). Etodolac is marketed as the racemate. The absolute configurations of the enantiomers were found to be S(+) and R(−), which is similar to that for most other NSAIDs. However, Demerson et al., *J. Med. Chem.*, 26, 1778 (1983) found that the S(+)-enantiomer of etodolac possessed almost all of the anti-inflammatory activity of the racemate, as measured by reduction in paw volume of rats with adjuvant polyarthritis, and prostaglandin synthetase inhibitory activity of the drug. No anti-inflammatory activity was discernible with the R(−) enantiomer, and it is not converted significantly to the S(+) enantiomer in vivo. Hence, R(−)-etodolac is not a NSAID. However, as disclosed below, R(−)-etodolac paradoxically was found to have potent activity against cancer cells that is at least equivalent to that of the S(+) enantiomer.

Etodolac possesses several unique disposition features due to their stereoselective pharmacokinetics. In plasma, after the administration of RS-etodolac, the concentrations of the "inactive" R-enantiomer of etodolac are about 10-fold higher than those of the active S-enantiomer, an observation that is novel among the chiral NSAIDs. See, D. R. Brocks et al., *Clin. Pharmacokinet.*, 26, 259 (1994). After a 200 mg dose in six elderly patients, the maximum plasma concentration of the R-enantiomer was about 33 μM. In contrast, the maximum concentration of the S-enantiomer was 5-fold lower. The typical dosage of the racemic mixture of etodolac is 400 mg BID, and the drug has an elimination half-life between 6-8 hours. Moreover, it is likely that the administration of the purified R-enantiomer will not display the side effects associated with cyclooxygenase (COX) inhibitors, such as ulcers and renal insufficiency, and thus can be given at considerably higher dosages. Nonetheless, the relatively low solubility of R(−)-etodolac in water can impede attaining plasma levels in humans that can inhibit cancer cells, particularly prostate cancer cells. However, the compounds of formula (I) can be dissolved in water and other aqueous carriers at substantially higher concentrations than R(−)-etodolac.

The compounds of formula (I) can also be prepared in the form of their pharmaceutically acceptable salts or their non-pharmaceutically acceptable salts. The non-pharmaceutically acceptable salts are useful as intermediates for the preparation of pharmaceutically acceptable salts. Pharmaceutically acceptable salts are salts that retain the desired biological activity of the parent compound and do not impart undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (b) salts formed from elemental anions such as chlorine, bromine, and iodine. Preferred carboxylic acid salts are those of hydrophilic amines, such as glucamine or N—($C_1$-$C_4$)alkylglucamine (see, Adger et al. (U.S. Pat. No. 5,811,558)).

The magnitude of a prophylactic or therapeutic dose of a compound or compounds of formula (I) in the acute or chronic management of cancer, i.e., prostate cancer, will vary with the type and/or stage of the cancer, the adjunct chemotherapeutic agent(s) or other anti-cancer therapy used, and the route of administration. The dose, and perhaps the dose frequency, will also vary according to the age, body weight, condition, and response of the individual patient. In general, the total daily dose range for a compound or compounds of formula (I), for the conditions described herein, is from about 50 mg to about 5000 mg, in single or divided doses. Preferably, a daily dose range should be about 100 mg to about 4000 mg, most preferably about 1000-3000 mg, in single or divided doses, e.g., 750 mg every 6 hr of orally administered compound. This can achieve plasma levels of about 500-750 μM, which can be effective to kill cancer cells. In managing the patient, the therapy should be initiated at a lower dose and increased depending on the patient's global response. It is further recommended that infants, children, patients over 65 years, and those with impaired renal or hepatic function initially receive lower doses, particularly of analogs which retain COX inhibitory activity, and that they be titrated based on global response and blood level. It may be necessary to use dosages outside these ranges in some cases. Further, it is noted that the clinician or treating physician will know how and when to interrupt, adjust or terminate therapy in conjunction with individual patient response. The terms "an effective inhibitory or amount" or "an effective sensitizing amount" are encompassed by the above-described dosage amounts and dose frequency schedule.

Any suitable route of administration may be employed for providing the patient with an effective dosage of a compound of formula (I). For example, oral, rectal, parenteral (subcutaneous, intravenous, intramuscular), intrathecal, transdermal, and like forms of administration may be employed. Dosage forms include tablets, troches, dispersions, suspensions, solutions, capsules, patches, and the like. The compound may be administered prior to, concurrently with, or after administration of chemotherapy, or continuously, i.e., in daily doses, during all or part of, a chemotherapy regimen. The compound, in some cases, may be combined with the same carrier or vehicle used to deliver the anti-cancer chemotherapeutic agent.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrated agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol.

Various other materials may be present as coatings or to otherwise modify the physical form of the solid unit dosage form. For instance, tablets, pills, or capsules may be coated with gelatin, wax, shellac or sugar and the like. Tablets, capsules, pills, granules, microparticles and the like can also comprise an enteric coating, such as a coating of one of the Eudragit® polymers, that will permit release of the active compound(s) in the intestines, not in the acidic environment of the stomach. This can be advantageous in the case of elderly or frail cancer patients treated with any compound that retains a significant COX-inhibitory activity, and concomitant ulceration.

A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a non-toxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, non-toxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

Due to the ability of compounds of formula (I) that elevate PPAR-γ levels, to lower the expression of the androgen receptor known to be overexpressed in hormone-refractory prostate cancer, compounds that upregulate PPAR-γ are advantageously used in combination with steroidal and non-steroidal anti-androgens used in the treatment of prostate cancer. These compounds include leuprolide or goserelin acetate, bicalutamide and flutamide, nilutamide, cycloproterone acetate, among others.

Due to the ability of compounds of formula (I) that reduce PPAR-γ levels to sensitize prostate cancer cells to killing by conventional chemotherapeutic agents, such compounds can be employed with chemotherapeutic agents used to treat cancers such as prostate cancer, including estramustine, vinblastine, mitoxanthrone, prednisone and the like, or melphalan to treat MM. Other chemotherapeutic agents, irradiation or other anti-cancer agents such as anti-tumor antibodies, or cytokines can be used with the present compounds. See, e.g., *Remington's Pharmaceutical Sciences* (18th ed. 1990) at pages 1138-1162.

The invention will be further described by reference to the following detailed examples.

Preparation of Compounds of the Invention

General Chemistry. Pharmaceutical-grade tablets of racemic etodolac were purchased from Watson Laboratories, Corona, Calif. All other reagents and solvents were acquired from Aldrich, Milwaukee, Wis. Uncorrected melting points were determined on a Laboratory Device Mel-Temp II capillary melting point apparatus. Proton nuclear magnetic resonance spectra were recorded on a Varian Unity 500 NMR spectrophotometer at 499.8 MHz or on a Varian Mercury NMR spectrophotometer at 400.06 MHz. The chemical shifts were reported in ppm on the δ scale from the indicated reference. Positive and negative ion loop mass spectra were performed by HT Laboratories, San Diego, Calif. Elemental analyses were performed by NuMega Resonance Labs, San Diego, Calif. Column chromatography was conducted on E Merck silica gel (230-400 mesh) with the indicated solvent system. Analytical thin layer chromatography (TLC) was conducted on silica gel 60 F-254 plates (EM Reagents).

EXAMPLE 1

2-(1,8-Diethyl-1,3,4,9-tetrahydropyrano[3,4-b]indol-1-yl)-ethanol (1)

A solution of etodolac (2.0 g, 6.97 mmol) in dry THF (5 mL) was added dropwise to 1M LiAlH$_4$ in THF (10.5 mL, 10.5 mmol, 1.5 eq) over five minutes and stirred at room temperature overnight under argon. The resulting mixture was then slowly quenched with EtOAc and poured over water to form an emulsion. The emulsion was filtered, and the aqueous layer was separated and extracted twice with EtOAc. The three organic phases were combined, washed with brine, dried with Na$_2$SO$_4$, concentrated, and purified by column chromatography using 50:50:EtOAc:Hexane to give a yellow oil (1.87 g, 98%): $^1$HNMR (CDCl$_3$, δ TMS): 0.95 (t, 3H), 1.36 (t, 3H), 1.96 (m, 2H), 2.14 (m, 2H), 2.68 (br, OH), 2.81 (m, 2H), 2.83 (q, 2H), 3.70 (m, 2H), 4.07 (m, 2H), 7.02-7.39 (m, 3H, Ar—H), 7.74 (br, 1H, NH). MS$^+$: m/z 296 (MNa$^+$). MS$^-$: m/z 308 (MCl$^-$), 272 ([M–H]$^-$).

EXAMPLE 2

1,8-Diethyl-1-(2-methoxyethyl)-1,3,4,9-tetrahydropyrano[3,4-b]indole (2)

To a solution of compound 1 (348 mg, 1.27 mmol) in dry THF (5 mL) under argon, 60% NaH in mineral oil (64 mg, 1.59 mmol, 1.25 eq) was added in a portion-wise manner. After stirring for thirty minutes, MeI (99 µL, 1.59 mmol, 1.25 eq) was added dropwise, and the reaction was stirred for 2 days at room temperature. The resulting mixture was diluted with brine and extracted three times with Et$_2$O. The combined organic phases were dried with Na$_2$SO$_4$, concentrated, and purified by column chromatography using 20:80:EtOAc:Hexane to give a yellow-white solid (228 mg, 62%): mp 125-126° C. $^1$HNMR (CDCl$_3$, δ TMS): 0.86 (t, 3H), 1.37 (t, 3H), 1.94 (m, 2H), 2.15 (m, 2H), 2.78 (t, 2H), 2.85 (q, 2H), 3.37 (s, 3H), 3.52 (m, 2H), 4.00 (m, 2H), 6.99-7.38 (m, 3H, Ar—H), 8.43 (br, 1H, NH). MS$^-$: m/z 286 ([M–H]$^-$). Anal. (C$_{18}$H$_{25}$NO$_2$): C, H, N.

EXAMPLE 3

1,8-Diethyl-1-(2-fluoroethyl)-1,3,4,9-tetrahydropyrano[3,4-b]indole (3)

To a stirred solution of compound 1 (136 mg, 0.5 mmol) in CH$_2$Cl$_2$ (2 mL) at –40° C. under argon, DAST (396 µL, 3.0 mmol, 6.0 eq) was slowly added in a dropwise manner. The resulting mixture was allowed to warm to room temperature and stirred for one hour before being cooled to 0° C. and quenched with MeOH (1 mL). The mixture was stirred an additional thirty minutes at room temperature, and then saturated NaHCO$_3$ (10 mL) was added dropwise. The resulting aqueous layer was extracted three times with CH$_2$Cl$_2$. The combined organic phases were dried with Na$_2$SO$_4$, concentrated, and purified by column chromatography using 5:95:EtOAc:Hexane to give a yellow-white solid (45 mg, 33%): mp 118-119° C. $^1$HNMR (CDCl$_3$, δ TMS): 0.88 (t, 3H), 1.37 (t, 3H), 1.94 (m, 2H), 2.29 (m, 2H), 2.78 (m, 2H), 2.86 (q, 2H), 3.99 (m, 2H), 4.57 (qq, 2H), 7.03-7.38 (m, 3H, Ar—H), 7.65 (br, 1H, NH). MS$^-$: m/z 310 (MCl$^-$), 274 ([M–H]$^-$). Anal. (C$_{17}$H$_{22}$NOF): C, H, N.

EXAMPLE 4

1-(2-Chloroethyl)-1,8-diethyl-1,3,4,9-tetrahydropyrano[3,4-b]indole (4)

A solution of compound 1 (136 mg, 0.5 mmol), PPh$_3$ (262 mg, 1.0 mmol, 2.0 eq), and CCl$_4$ (2.5 mL) was refluxed overnight. The resulting mixture was then diluted with water and extracted three times with CH$_2$Cl$_2$. The organic phases were combined, dried with Na$_2$SO$_4$, concentrated, and purified by column chromatography using 5:95:EtOAc:Hexane to give a white solid (74 mg, 51%): mp 106-107° C. (dec). $^1$HNMR (CDCl$_3$, δ TMS): 0.93 (t, 3H), 1.37 (t, 3H), 1.91 (m, 2H), 2.34 (m, 2H), 2.76 (m, 2H), 2.87 (q, 2H), 3.46 (dm, 2H), 3.99 (m, 2H), 7.04-7.38 (m, 3H, Ar—H), 7.55 (br, 1H, NH). MS$^-$: m/z 326 (MCl$^-$), 290 ([M–H]$^-$). Anal. (C$_{17}$H$_{22}$NOCl): C, H, N.

EXAMPLE 5

1,1,8-Triethyl-1,3,4,9-tetrahydropyrano[3,4-b]indole (5)

To a stirred solution of compound 4 (103 mg, 0.35 mmol), AIBN (11 mg, 0.07 mmol, 0.2 eq), and toluene (3 mL) at room temperature under argon, HSnBu$_3$ (380 µL, 1.41 mmol, 4.0 eq) was added in a dropwise manner. The resulting mixture was stirred overnight at 110° C. and concentrated. The residue was diluted with hexane and extracted three times with acetonitrile. The acetonitrile layers were combined, concentrated, and purified by column chromatography using 3:97:EtOAc:Hexane to give an off-white solid (56 mg, 62%): mp 133-134° C. $^1$HNMR (CDCl$_3$, δ TMS): 0.88 (t, 6H), 1.37 (t, 3H), 1.87 (q, 4H), 2.78 (t, 2H), 2.86 (q, 2H), 4.02 (t, 2H), 7.01-7.38 (m, 3H, Ar—H), 7.46 (br, 1H, NH). MS$^-$: m/z 256 ([M–H]$^-$). Anal. (C$_{17}$H$_{23}$NO): C, H, N.

EXAMPLE 6

2-(1,8-Diethyl-1,3,4,9-tetrahydropyrano[3,4-b]indol-1-yl)-acetamide (6)

To a stirred solution of etodolac (287 mg, 1.0 mmol) in CH$_2$Cl$_2$ (5 mL) at room temperature, oxalyl chloride (105 µL, 1.2 mmol, 1.2 eq) was added dropwise, followed by a catalytic amount of DMF (2 drops). The mixture was stirred for one hour and then concentrated. The resulting orange solid was dissolved in dry THF (2 mL) and added dropwise to a stirred solution of ice-cold concentrated NH$_4$OH (5 mL). The mixture was allowed to warm to room temperature, stirred for two days, diluted with brine, and extracted three times with EtOAc. The combined organic phases were dried with Na$_2$SO$_4$, concentrated, and purified by column chromatography using 50:50:EtOAc:Hexane to give a yellow-white solid (100 mg, 35%): mp 189-190° C. $^1$HNMR (CDCl$_3$, δ TMS): 0.87 (t, 3H), 1.32 (t, 3H), 2.08 (m, 2H), 2.83 (m, 4H), 2.91 (q, 2H), 4.07 (m, 2H), 5.48 (br, 1H, CONH$_2$), 6.33 (br, 1H, CONH$_2$), 6.99-7.36 (m, 3H, Ar—H), 9.26 (br, 1H, NH). MS$^+$: m/z 309 (MNa$^+$). MS$^-$: m/z 321 (MCl$^-$), 286 (M$^-$). Anal. (C$_{17}$H$_{22}$N$_2$O$_2$.0.125H$_2$O): C, H, N.

EXAMPLE 7

2-(1,8-Diethyl-1,3,4,9-tetrahydropyrano[3,4-b]indol-yl)-ethylideneamine (7)

A solution of compound 6 (119 mg, 0.42 mmol) in dry THF (3 mL) was added dropwise to 1M LiAlH$_4$ in THF (624 µL, 0.62 mmol, 1.5 eq) and stirred for two hours at room temperature under argon. Another equivalent of 1M LiAlH$_4$ in THF (420 µL, 0.42 mmol, 1.0 eq) was then added and the reaction was stirred overnight. The resulting mixture was then slowly quenched with EtOAc and poured over water to form an emulsion. The emulsion was filtered, and the aqueous layer was separated and extracted twice with EtOAc. The three organic phases were then combined, dried with Na$_2$SO$_4$, concentrated, and purified by column chromatography using 50:50:EtOAc:Hexane to give a yellow-brown solid (40 mg, 36%): mp 101-103° C. $^1$HNMR (CDCl$_3$, δ TMS): 0.94 (t, 3H), 1.38 (t, 3H), 1.96 (m, 2H), 2.73 (qd, 2H), 2.87 (q, 2H), 2.99 (t, 2H), 3.32 (m, 1H, CH═N), 3.87 (t, 2H), 7.04-7.43 (m, 3H, Ar—H), 7.89 (br, 1H, NH). MS$^+$: m/z 293 (MNa$^+$), 271 (MH$^+$). MS$^-$: m/z 269 ([M–H]$^-$). Anal. (C$_{17}$H$_{22}$N$_2$O.0.5H$_2$O): C, H, N.

EXAMPLE 8

(1,8-Diethyl-1,3,4,9-tetrahydropyrano[3,4-b]indol-1-yl)-acetaldehyde (8) and 1,8-Diethyl-1-(2-methylsufanylmethoxyethyl)-1,3,4,9-tetrahydropyrano[3,4-b]indole (9)

A solution of compound 1 (136 mg, 0.5 mmol), dry DMSO (1.5 mL), and dry Ac$_2$O (1.0 mL) was stirred overnight at room temperature. The reaction mixture was then diluted with water and extracted three times with $Et_2O$. The combined organic phases were washed with saturated $NaHCO_3$, dried with $Na_2SO_4$, concentrated, and purified by column chromatography using 10:90:EtOAc:Hexane to give compound 8 (yellow-white solid, 72 mg, 53%) and compound 9 (yellow oil, 60 mg, 36%).

For compound 8, mp 123-124° C. $^1$HNMR ($CDCl_3$, δ TMS): 0.87 (t, 3H), 1.37 (t, 3H), 2.04 (m, 2H), 2.81 (m, 2H), 2.87 (q, 2H), 3.07 (s, 2H), 4.02 (m, 2H), 7.03-7.38 (m, 3H, Ar—H), 8.36 (br, 1H, NH), 9.78 (s, 1H, CHO). $MS^-$: m/z 270 ([M–H]$^-$). TLC (20:80:EtOAc:Hexane): Rf(7)=0.37. Anal. ($C_{17}H_{21}NO_2.0.1C_4H_8O_2.0.1C_6H_{14}.0.75H_2O$): C, H, N.

For compound 9, $^1$HNMR ($CDCl_3$, δ TMS): 0.88 (t, 3H), 1.36 (t, 3H), 1.94 (m, 2H), 2.14 (s, 3H), 2.20 (m, 2H), 2.79 (t, 2H), 2.86 (q, 2H), 3.66 (dq, 2H), 4.06 (q, 2H), 4.62 (s, 2H), 7.01-7.38 (m, 3H, Ar—H), 8.21 (br, 1H, NH). $MS^-$: m/z 332 ([M–H]$^-$). TLC (20:80:EtOAc:Hexane): Rf(8) =0.46. Anal. ($C_{19}H_{27}NO_2S.0.5H_2O$): C, H, N.

When the reaction mixture is allowed to stir overnight at 50° C. compound 9 was afforded as the major product.

EXAMPLE 9

Alternative synthetic method for (1,8-Diethyl-1,3,4, 9-tetrahydropyrano[3,4-b]indol-1-yl)-acetaldehyde (8)

To a stirred solution of compound 1 (136 mg, 0.5 mmol), $CH_2Cl_2$ (2 mL), dry DMSO (142 μL, 2.0 mmol, 4.0 eq), and dry TEA (697 μL, 5.0 mmol, 10.0 eq) at room temperature under argon, sulfur trioxide-pyridine complex (Pyr-$SO_3$, 318 mg, 2.0 mmol, 4.0 eq) was added in a portion-wise manner and stirred for two days. The resulting mixture was then diluted with water and extracted three times with $Et_2O$. The combined organic phases were dried with $Na_2SO_4$, concentrated, and purified by column chromatography using 20:80: EtOAc:Hexane to give a yellow-white solid (70 mg, 52%). Spectral data were identical to those reported above.

EXAMPLE 10

Acetic acid-2-(1,8-diethyl-1,3,4,9-tetrahydropyrano [3,4-b]indol-1-yl)-ethyl ester (10)

A solution of compound 1 (273 mg, 1.0 mmol), dry DMSO (3 mL), dry $Ac_2O$ (2 mL), and dry TEA (1 mL) was stirred overnight at room temperature. The reaction mixture was then diluted with water and extracted three times with EtOAc. The combined organic phases were washed with saturated $NaHCO_3$ and brine, dried with $Na_2SO_4$, concentrated, and purified by column chromatography using 10:90: EtOAc:Hexane to give a yellow solid (245 mg, 78%): mp 126-127° C. $^1$HNMR ($CDCl_3$, δ TMS): 0.91 (t, 3H), 1.38 (t, 3H), 1.88 (s, 3H), 1.90 (m, 2H), 2.21 (t, 2H), 2.78 (m, 2H), 2.87 (q, 2H), 4.01 (t, 2H), 4.14 (m, 2H), 7.02-7.37 (m, 3H, Ar—H), 7.71 (br, 1H, NH). $MS^-$: m/z 350 ($MCl^-$), 314 ([M–H]$^-$). Anal. ($C_{19}H_{25}NO_3$): C, H, N.

EXAMPLE 11

2-(1,8-Diethyl-1,3,4,9-tetrahydropyrano[3,4-b]indol-1-yl)-ethane-1,1-diol (11)

Dry DMSO (71 μL, 1.0 mmol, 2.0 eq) was added dropwise to a solution of oxalyl chloride (66 μL, 0.75 mmol, 1.5 eq) in $CH_2Cl_2$ (1 mL) at −78° C. After stirring for ten minutes, a solution of compound 1 (136 μL, 0.5 mmol) in $CH_2Cl_2$ (4 mL) was added dropwise, and the reaction was stirred for an additional thirty minutes at −78° C. before the addition of TEA (2.79 μL, 2.0 mmol, 4.0 eq). The reaction mixture was then allowed to warm slowly to 0° C., diluted with saturated $NH_4Cl$, and extracted twice with $Et_2O$. The combined organic phases were washed with water and brine, dried with $Na_2SO_4$, concentrated, and purified by column chromatography using a gradient of 50:50:EtOAc:Hexane to 100% EtOAc to give a white solid (46 mg, 32%): mp 158-159° C. $^1$HNMR ($CDCl_3$, δ TMS): 0.50 (t, 3H), 1.25 (t, 3H), 1.50 (m, 1H), 1.82 (m, 1H), 2.04 (m, 1H), 2.17 (m, 1H), 2.33 (m, 1H), 2.58 (q, 2H), 2.88 (m, 2H), 3.77 (m, 1H), 3.91 (m, 1H), 4.19 (q, 1H), 4.33 (m, 1H), 7.02-7.15 (m, 3H, Ar—H), 7.66 (br, 1H, NH). $MS^-$: m/z 288 ([M–H]$^-$). Anal. ($C_{17}H_{23}NO_3$): C, H, N.

EXAMPLE 12

1-(1,8-Diethyl-1,3,4,9-tetrahydropyrano[3,4-b]indol-1-yl)-propan-2-ol (12)

A solution of compound 8 (275 mg, 1.01 mmol) in dry THF (4 mL) was added dropwise over five minutes to a stirred solution of 1M MeMgCl in THF (1.52 mL, 1.52 mmol, 1.5 eq) at 0° C. under argon and allowed to warm slowly to room temperature. After stirring for two hours, another equivalent of 3M MeMgCl in THF (337 μL, 1.01 mmol, 1.0 eq) was added, and the mixture was stirred for an additional hour. The mixture was then diluted with saturated $NaHCO_3$ and extracted three times with EtOAc. The combined organic phases were dried with $Na_2SO_4$, concentrated, and purified by column chromatography using 20:80: EtOAc:Hexane to give a yellow solid (280 mg, 96%): mp 103-104° C. $^1$HNMR ($CDCl_3$, δ TMS) shows a 2:1 mixture of diastereomers. $MS^-$: m/z 322 ($MCl^-$), 286 ([M–H]$^-$). Anal. ($C_{18}H_{25}NO_2$): C, H, N. The product was carried on to the next step as a mixture of diastereomers.

EXAMPLE 13

1-(1,8-Diethyl-1,3,4,9-tetrahydropyrano[3,4-b]indol-1-yl)-propan-2-one (13)

To a solution of compound 12 (77 mg, 0.27 mmol), $CH_2Cl_2$ (2 mL), dry DMSO (76 μL, 1.07 mmol, 4.0 eq), and dry TEA (374 μL, 2.68 mmol, 10.0 eq) at room temperature under argon, sulfur trioxide-pyridine complex (Pyr-$SO_3$, 171 mg, 1.07 mmol, 4.0 eq) was added in a portion-wise manner and stirred overnight. The resulting mixture was then diluted with brine and extracted three times with EtOAc. The combined organic phases were dried with $Na_2SO_4$, concentrated, and purified by column chromatography using 15:85: EtOAc:Hexane to give an off-white solid (39 mg, 51%): mp 154-155° C. $^1$HNMR ($CDCl_3$, δ TMS): 0.80 (t, 3H), 1.37 (t, 3H), 2.02 (m, 2H), 2.21 (s, 3H), 2.78 (m, 2H), 2.88 (q, 2H), 3.14 (s, 2H), 3.98 (m, 2H), 7.01-7.37 (m, 3H, Ar—H), 9.01 (br, 1H, NH). $MS^-$: m/z 284 ([M–H]$^-$). Anal. ($C_{18}H_{23}NO_2$): C, H, N.

EXAMPLE 14

Isolation of Racemic Etodolac (1,8-Diethyl-1,3,4,9-tetrahydropyrano[3,4-b]indole-1-acetic acid)

Pharmaceutical-grade tablets of racemic etodolac (20× 400 mg) were crushed to a fine powder with a mortar and pestle. The powder was then stirred in hot EtOAc (150 mL) for ten minutes and vacuum filtered through a Buchner funnel. This process was repeated two more times, and the three filtrates were combined and concentrated to give an off-white solid (7.92 g, 99%): $^1$HNMR (DMSO, δ TMS): 0.61 (t, 3H), 1.24 (t, 3H), 2.03 (q, 2H), 2.63 (m, 2H), 2.82 (dd, 2H), 2.83 (q, 2H), 3.92 (m, 2H), 6.86-7.23 (m, 3H, Ar—H), 10.47 (br, 1H, NH), 12.00 (br, COOH).

EXAMPLE 15

Sensitivity of Normal Peripheral Blood Lymphocytes and CLL Cells to Etodolac

Mononuclear cells were isolated from the peripheral blood of B-CLL patients and normal donors using density gradient centrifugation (Ficoll-Paque). Cells were cultured at $2 \times 10^6$ cells per mL in RPMI with 20% autologous plasma in 96-well plates with or without the indicated μM concentrations of etodolac (racemic, S-etodolac, R-etodolac) and in combination with 2-chloro-2N-deoxyadenosine (2CdA) or fludarabine. At indicated times (12, 24, 36, 48, 60, 72 hours), viability assays were performed using the erythrocin B exclusion assay, as described by D. Carson et al., *PNAS USA*, 89, 2970 (1992).

As shown in FIG. 1, significant death of normal PBLs occurred only at 800 μM racemic etodolac, a concentration which cannot be obtained in vivo.

Figure 2:
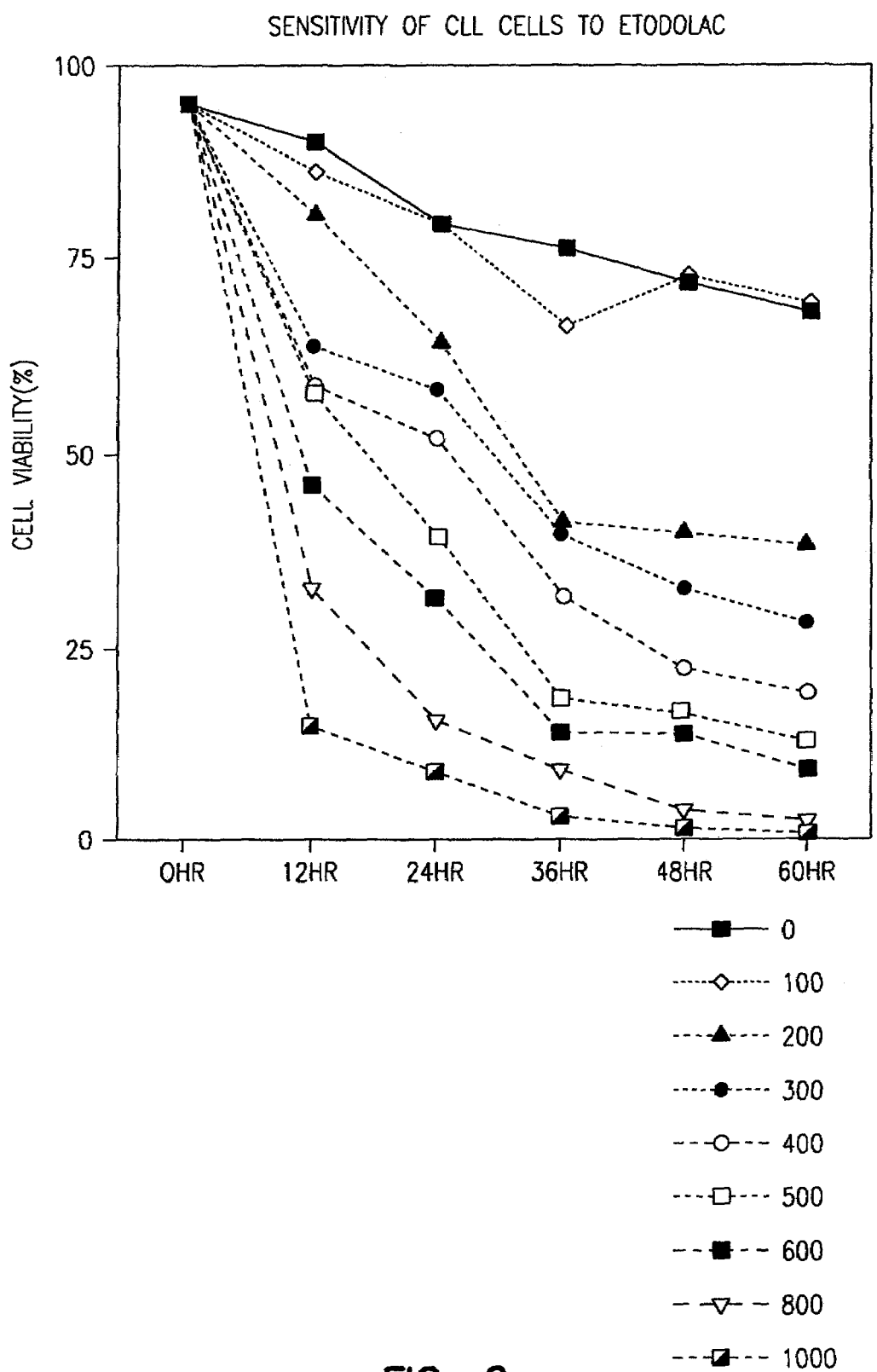
FIG. 2 is a graph depicting the sensitivity of CLL cells to racemic etodolac.

Peripheral blood lymphocytes from a normal donor were cultured with 1.0 mM etodolac for 24 hours. Then B lymphocytes were identified by staining with anti-CD19 antibody, and viability was assessed by $DiOC_6$ fluorescence. Etodolac under these conditions did not reduce the viability of the normal B cells, compared to control cultures. When the same viability assay was run with purified CLL cells from the peripheral blood of a CLL patient, the results were different. As shown in FIG. 2, 50% of the CLL cells were killed by a 48 hour exposure to 200 μM racemic etodolac. More than 95% of the treated cells were malignant B lymphocytes.

EXAMPLE 16

Synergistic Combinations of Etodolac and Chemotherapeutic Agents

Figure 3:
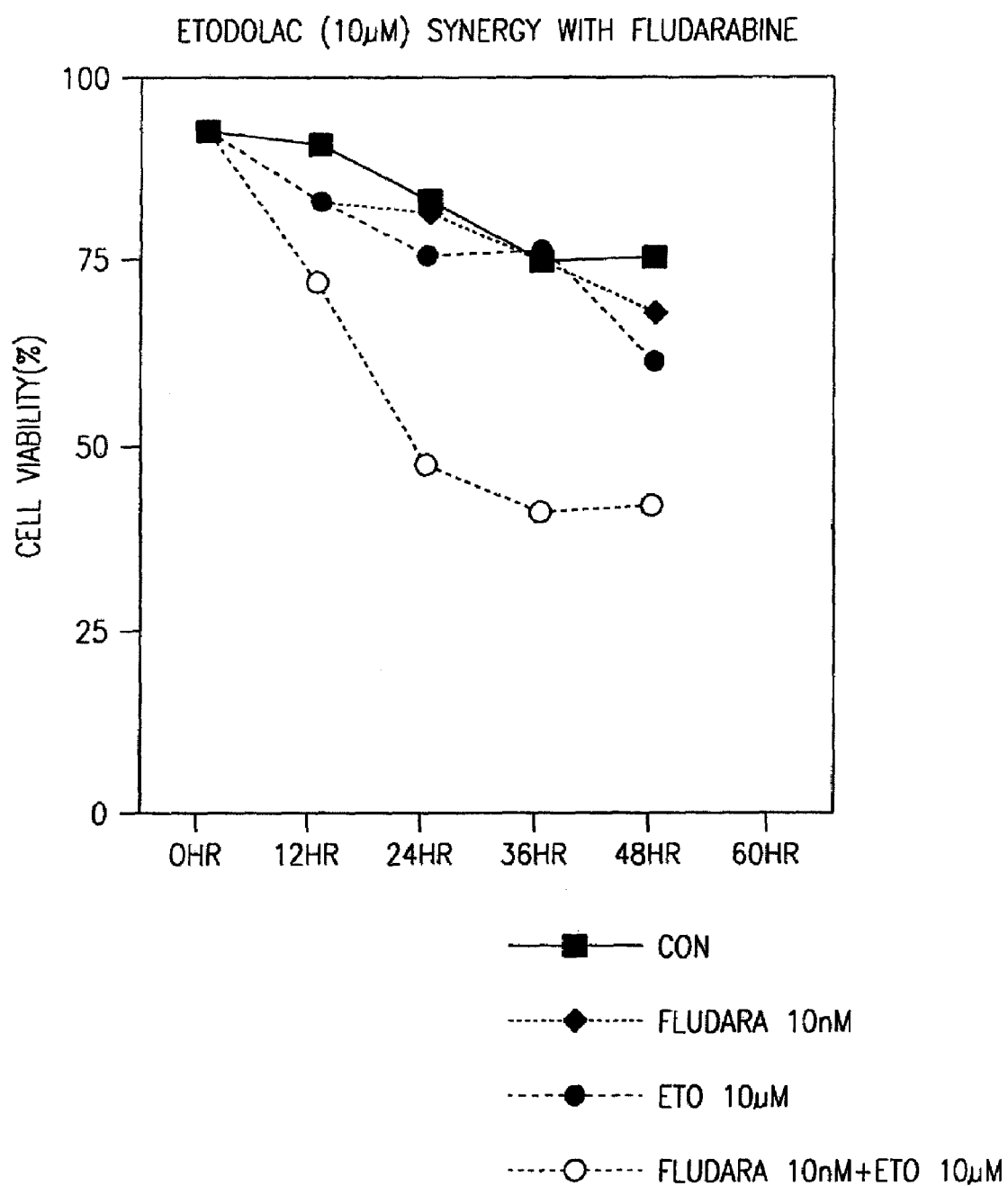
FIG. 3 is a graph depicting the synergistic effect of a combination of racemic etodolac and fludarabine against CLL cells.
Figure 4:
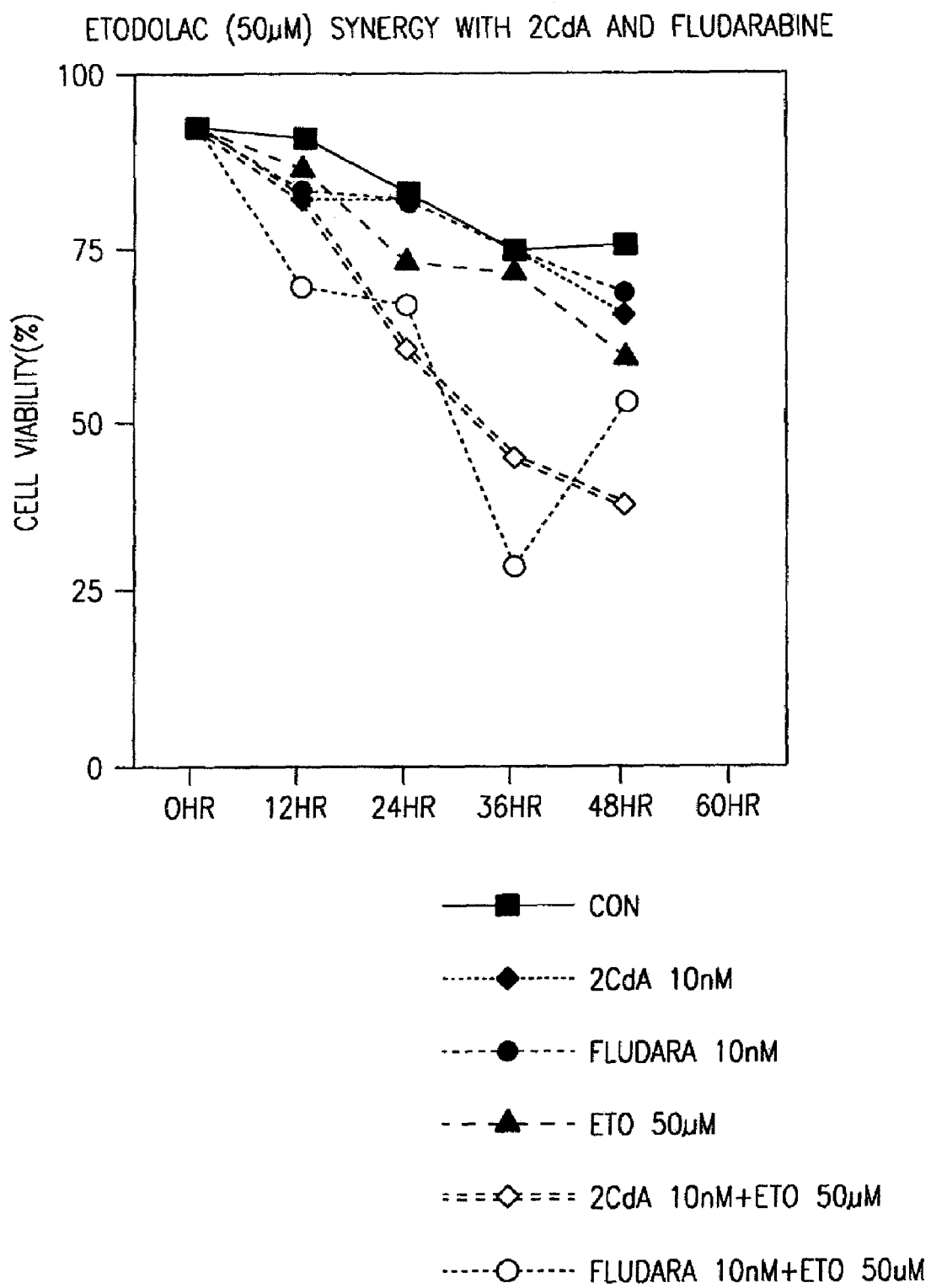
FIG. 4 is a graph depicting the synergistic effect of a combination of 50 μM etodolac with 10 μM 2CdA or 10 mM Fludara against CLL cells.

Fludarabine is a nucleoside analog commonly used for the treatment of CLL. In this experiment the in vitro survival of CLL cells at the indicated time points was compared in cultures containing medium alone ("Con", squares), fludarabine 10 nM (diamonds), etodolac 10 μM (closed circles), and fludarabine 10 nM plus etodolac 10 μM (open circles). The two drugs together exhibited a synergistic cytotoxic effect. FIG. 3 shows that the combination killed 50% of CLL cells during 48 hours of culture, while either drug alone was ineffective. FIG. 4 demonstrates synergy between 50 μM etodolac and 10 nM 2-chlorodeoxy-adenosine and fludarabine, under the same test conditions.

EXAMPLE 17

Effect of R(−) and S(+) Etodolac Against CLL Cells

Etodolac tablets were ground in a mortar and extracted from the formulation using ethyl acetate. The resulting racemic mixture of enantiomers was separated into R and S isomers on a preparative scale by fractional crystallization by the procedure of Becker-Scharfenkamp and Blaschke, *J. Chromatog.*, 621, 199 (1993). Thus, the racemic mixture solid was dissolved in absolute 2-propanol and S-1-phenyl-ethylamine was added to the solution. The resulting salt solution was stored in the refrigerator for 4 days. The crystalline white salt product was filtered and washed with cold 2-propanol and recrystallized two more times from 2-propanol. The same procedure was repeated for the R isomer only using R-1-phenylethylamine as the resolving agent. Finally, the R and S salts were decomposed using 10% sulfuric acid (v/v) and extracted with ethyl acetate. The chiral purity of each isomer was verified by HPLC using a Chiral-AGP column from ChromTech.

Figure 5:
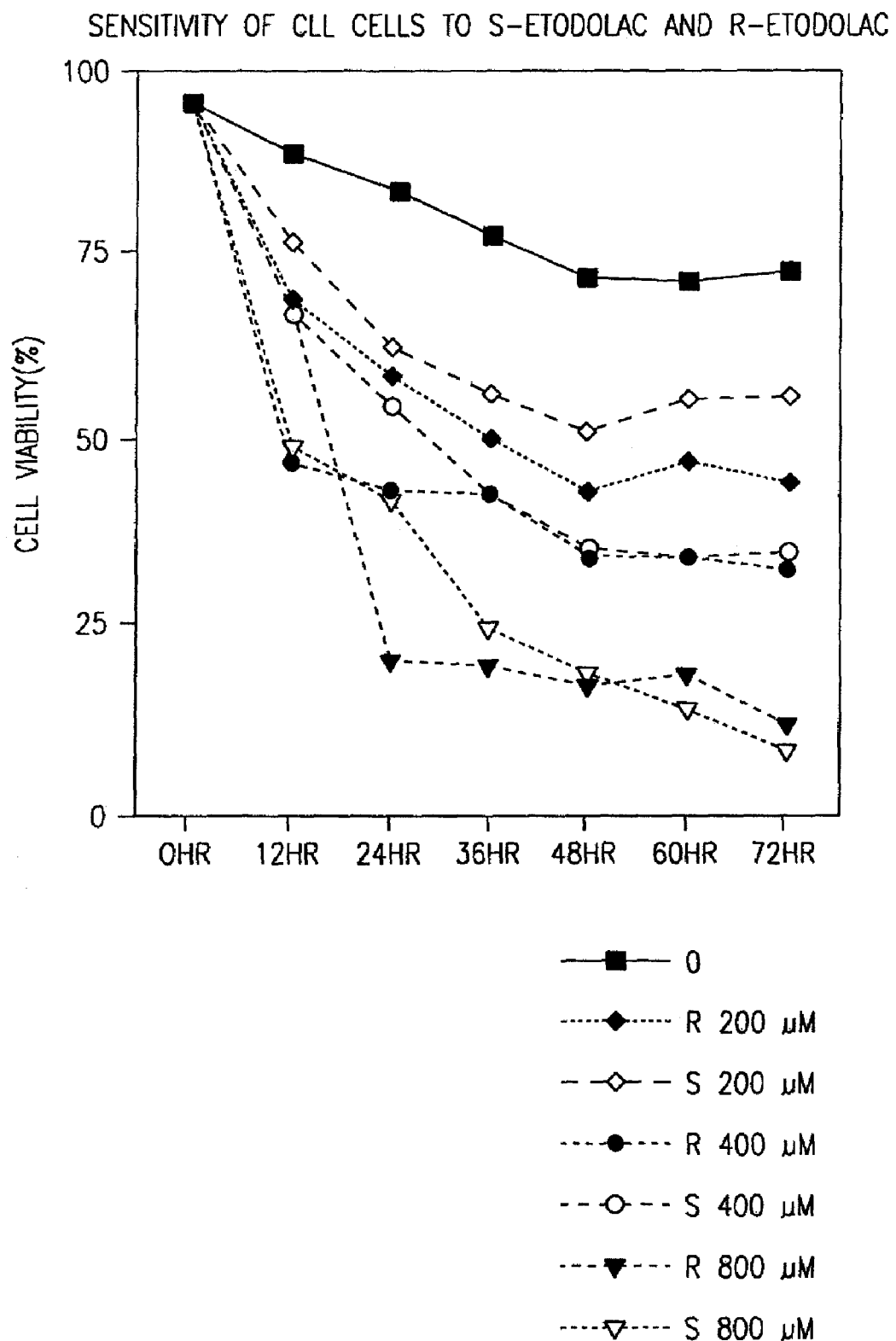
FIG. 5 is a graph depicting the sensitivity of CLL cells to S- and R-etodolac.

The toxicities of the two enantiomers to CLL cells cultured in RPMI 1640 medium with 10% autologous plasma were compared at the indicated concentrations and time points, as shown in FIG. 5. The R- and S-enantiomers are equivalently cytotoxic to the CLL cells.

EXAMPLE 18

Viability of CLL Cells Before and After Etodolac Treatment

Figure 6:
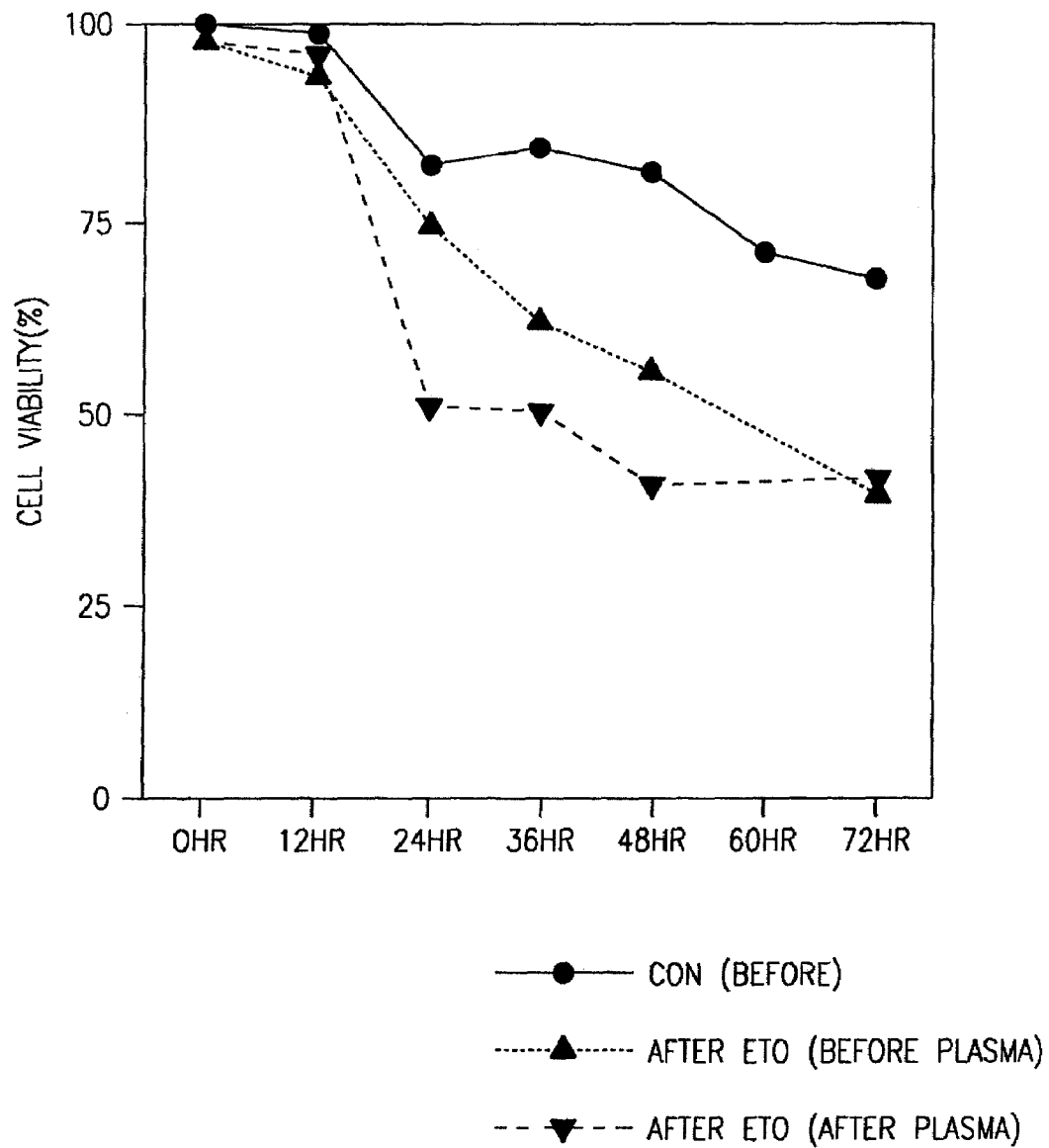
FIGS. 6 and 7 depict the viability of CLL cells from two patients before and after etodolac administration.
Figure 7:
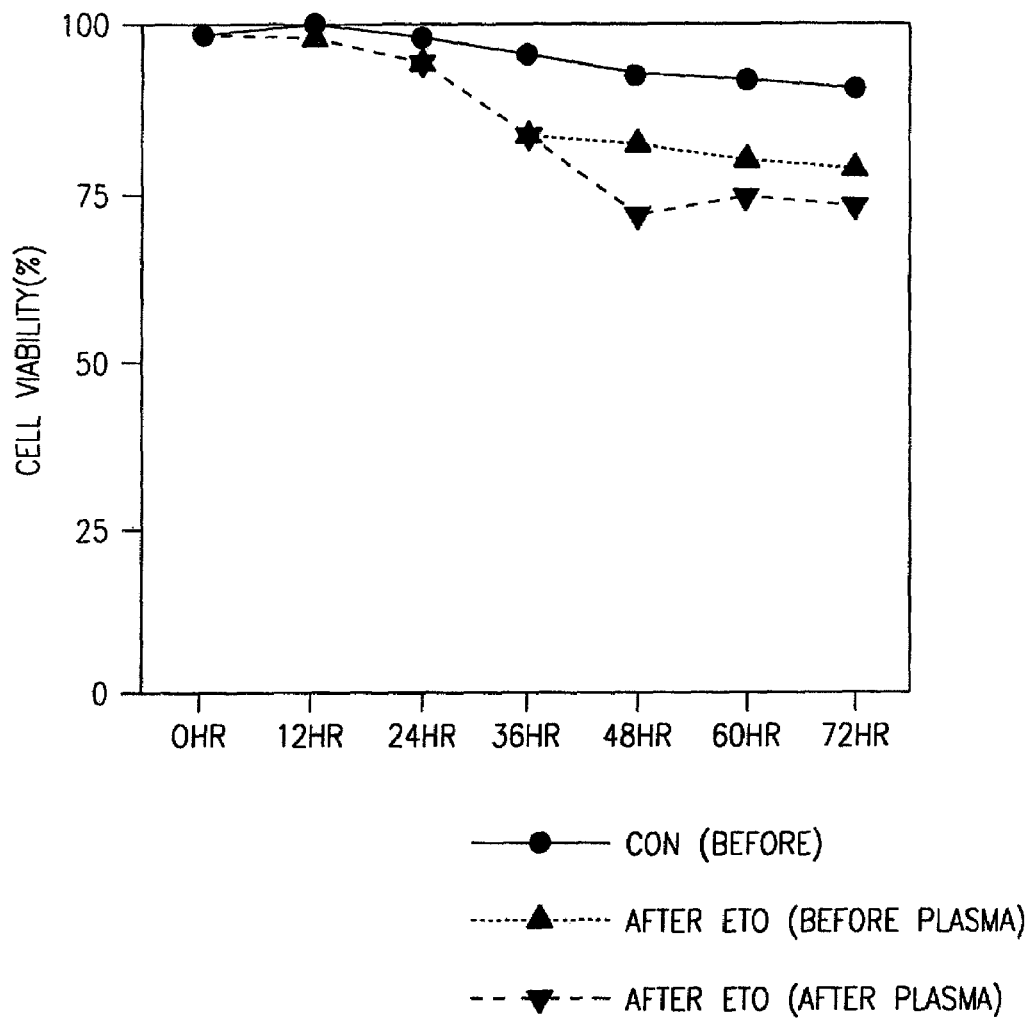
Figure 8A:
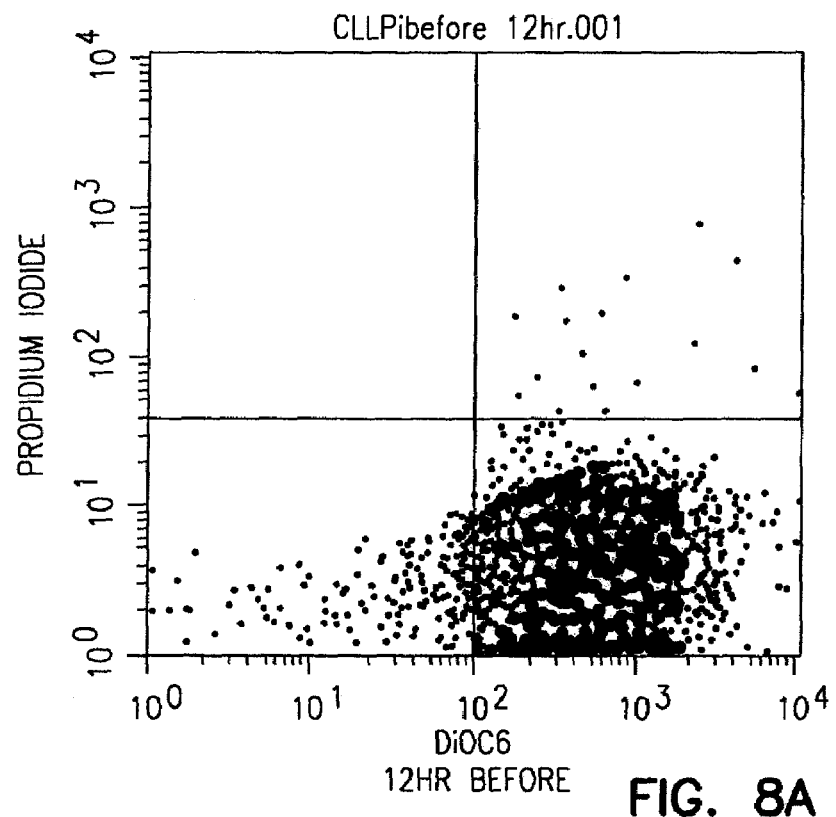
FIGS. 8A-8D depict a flow cytometric analysis of CLL cells before and after etodolac treatment.
Figure 8B:
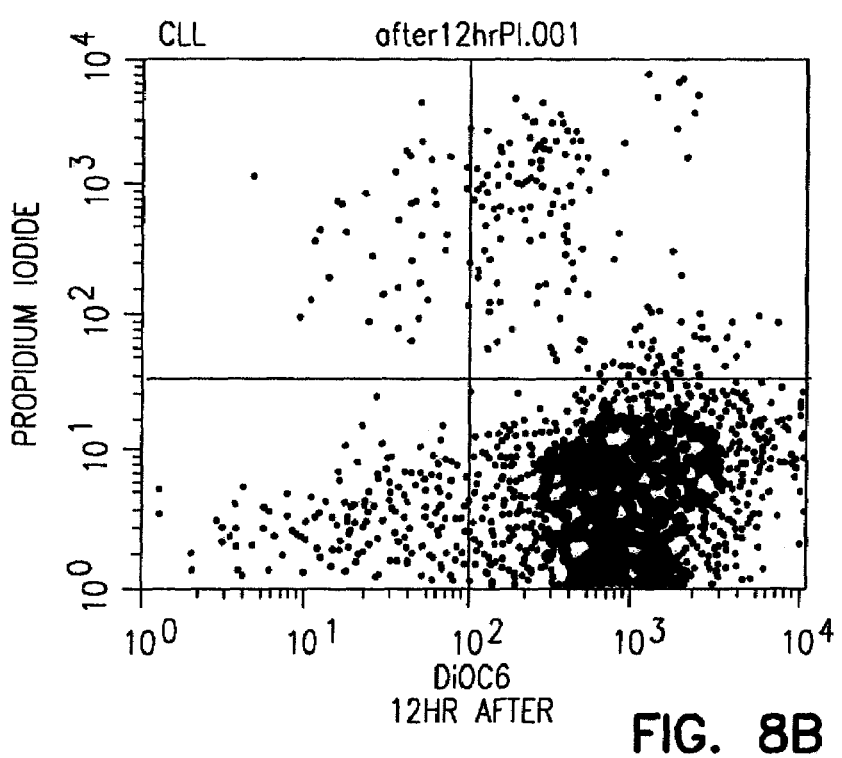
Figure 8C:
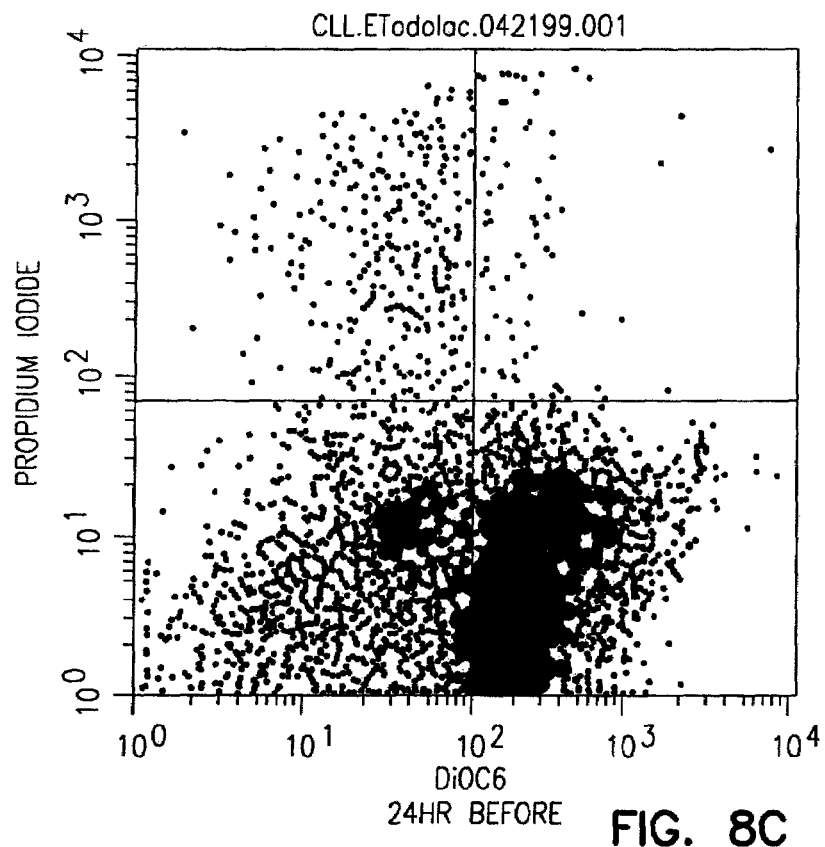
Figure 8D:
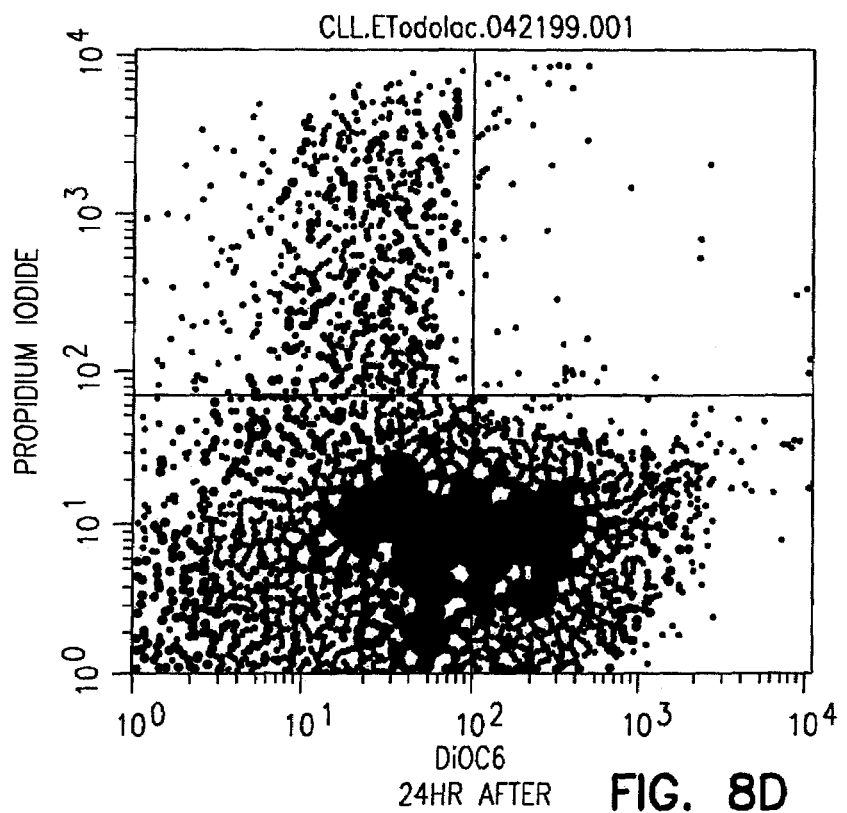

Heparinized blood was taken from two patients (JK and NA) with CLL. Then each patient immediately took a 400 mg etodolac tablet, and a second tablet 12 hours later. After another 12 hours, a second blood specimen was obtained. The CLL cells were isolated and their survival in vitro were compared in RPMI 1640 medium containing 10% autologous plasma, as described in Example 1. The circles show CLL cells before etodolac treatment. In FIGS. 6-7, the upward pointing triangles represent CLL cell viability after etodolac treatment, wherein the cells are dispersed in medium containing the pretreatment plasma. The downward pointing triangles are CLL cells after treatment maintained in medium with the post-treatment plasma.

FIG. 6 shows the different survivals of the two cell populations from patient JK. Note that the cells after treatment had a shortened survival compared to the cells before treatment. FIG. 7 shows a less dramatic but similar effect with patient NA. FIG. 8 is a flow cytometric analysis of CLL cells from patient JK before and after etodolac treatment. $DiOC_6$ is a dye that is captured by mitochondria. When cells die by apoptosis, the intensity of staining decreases. The X axis on the four panels in FIG. 8 shows the $DiOC_6$ staining. An increased number of dots in the left lower box indicates cell death by apoptosis. If one compares the cells taken from the patient before etodolac treatment, and after etodolac treatment, one can see that the number of dots in the left lower box is much higher after the drug. This effect is detectable at 12 hours, and increases further after 24 hours.

To conduct the flow cytometric analysis, the mitochondrial transmembrane potential was analyzed by 3,3' dihexyloxacarboncyanide iodide ($DiOC_6$), cell membrane permeability by propidium iodide (PI)[3] and mitochondrial respiration by dihydrorhodamine 123 (DHR) (See J. A. Royall et al., *Arch. Biochem. Biophys.*, 302, 348 (1993)). After CLL cells were cultured for 12 or 24 hours with the indicated amount of etodolac, the cells were incubated for 10 minutes at 37° C. in culture medium containing 40 nM of $DiOC_6$ and 5 μg/ml PI. Cells were also cultured for 3 hours with the indicated amount of etodolac, spun down at 200×g for 10 minutes and resuspended in fresh respiration buffer (250 mM sucrose, 1 g/L bovine serum albumin, 10 mM $MgCl_2$, 10 mM K/Hepes, 5 mM $KH_2PO_4$ (pH 7.4)) and cultured for 10 minutes at 37° C. with 0.04% digitonin. Then cells were loaded for 5 minutes with 0.1 µM dihydrorhodamine (DHR). Cells were analyzed within 30 minutes in a Becton Dickinson FAC-Scalibur cytofluorometer. After suitable comprehension, fluorescence was recorded at different wavelength: $DiOC_6$ and DHR at 525 nm (Fl-1) and PI at 600 nm (FL-3).

As a general matter a reduction of 10% in the survival of the post-treatment malignant cells, compared to the pretreatment malignant cells, at 16 hours after culture in vitro is considered a "positive" in this test, and indicates the use of etodolac, i.e., R(−)-etodolac in CLL or other cancer therapy.

EXAMPLE 19

Ability of R(−)-Etodolac to Selectively Kill MM Cells

Figure 9:
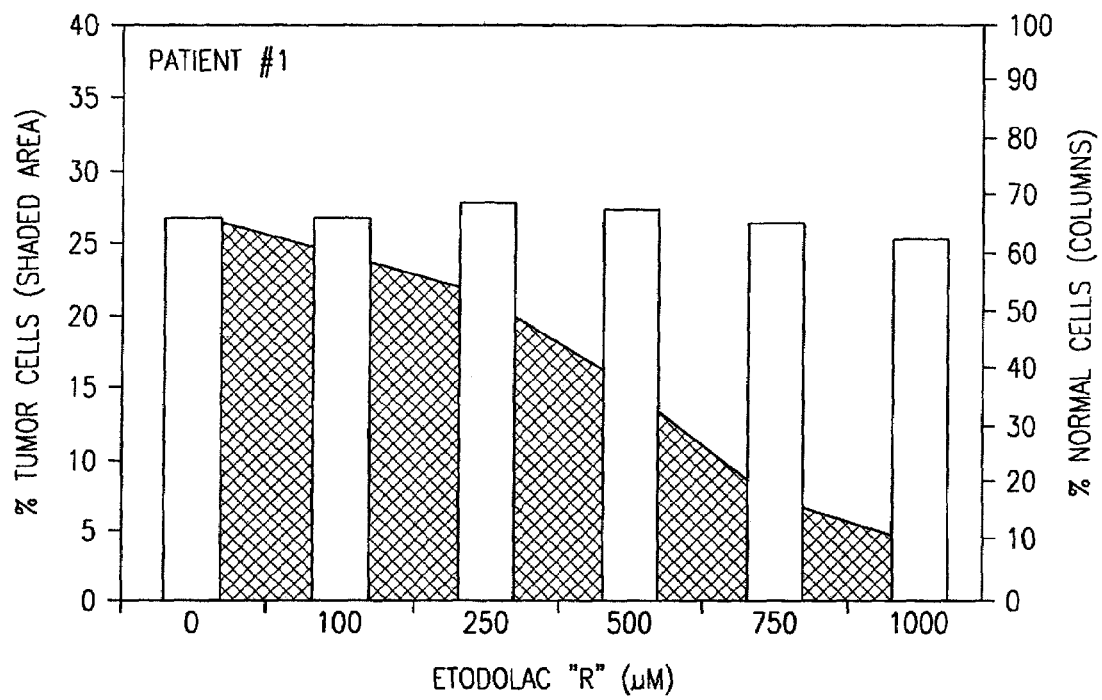
FIGS. 9 and 10 depict the selective action of R(-)-etodolac against MM cells from two patients.
Figure 10:
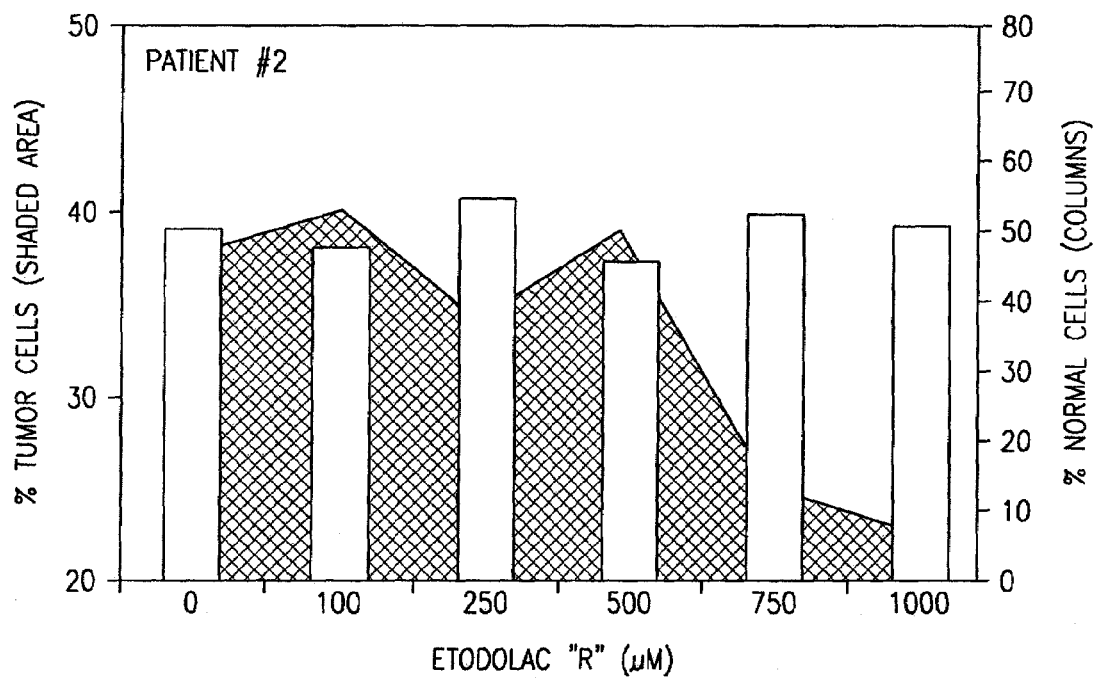

Bone marrow was obtained from two patients with multiple myeloma. The marrow contained a mixture of malignant cells, as enumerated by high level expression of the CD38 membrane antigen, and normal cells. The suspended marrow cells were incubated for 72 hours in RPMI 1640 medium with 10% fetal bovine serum, and various concentrations of the purified R-enantiomer of etodolac. Then the dead cells were stained with propidium iodide, and the multiple myeloma cells were stained with fluorescent monoclonal anti-CD38 antibodies. The data were analyzed by fluorescent activated cell sorting. FIGS. 9-10 show that R-etodolac did not kill the normal bone marrow cells (light bars), but dose-dependently killed the multiple myeloma cells (dark shaded areas), in the marrow cells from both patients.

EXAMPLE 20

Etodolac Cytotoxicity to Cancer Cell Lines

Table 1 summarizes the cytotoxic effects of R(−)-etodolac toward prostate cancer cell lines and one colon cancer cell line are indeed within clinically achievable concentrations, given that a 1 gram dosage of R(−)-etodolac should yield a maximal plasma concentration in a human subject of about 400 µM. The fact that the R(−)- and S(+)-enantiomers are both cytotoxic indicates that the anti-prostate cancer activity is COX independent. Note that R(−)-etodolac, which is devoid of anti-inflammatory activity, nonetheless is more toxic to prostate cancer cells than is S(+) etodolac.

TABLE 1

| Cell line | Origin | Etodolac R/S | Etodolac R | Etodolac S | Phenotype |
|---|---|---|---|---|---|
| PC-3 | Prostate | 340 ± 20* | 150 ± 15* | 800 + 30* | Sensitive |
| LNCaP-FGC | Prostate | 400 ± 35 | 270 ± 50 | 220 ± 20 | Sensitive |
| Alva-31 | Prostate | >1000 | >1000 | >1000 | Resistant |
| OVCAR-3 | Ovarian | >1000 | >1000 | >1000 | Resistant |
| MDA-MB-231 | Breast | >1000 | >1000 | >1000 | Resistant |
| HCT-116 | Colon | 450 ± 15 | 280 ± 20 | 420 ± 50 | Sensitive |
| SW260 | Colon | 1000 ± 120 | ND | ND | Resistant |
| A549 | Lung | >1000 | >1000 | >1000 | Resistant |

*$IC_{50}$ (µM) of Etodolac R/S, R or S. Cytotoxicity was assessed by MTT assay after three days continuous exposure to decreasing concentrations of the agent. The results were confirmed by FACS using propidium iodide uptake.

EXAMPLE 21

Etodolac Downregulation of Mcl-1 and Bag-1

Figure 11A:
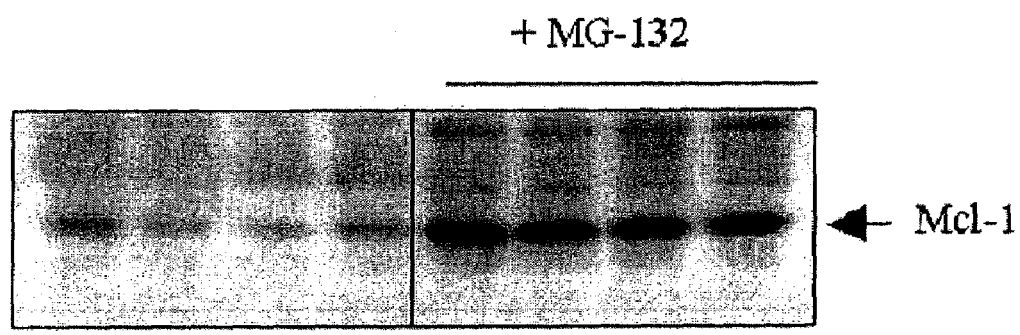
FIGS. 11A and 11B are a copies of a SDS-PAGE gels demonstrating that etodolac induces a rapid downregulation in Mcl-1 (Panel A) and Bag-1 (Panel B), that is blocked by MG-132.
Figure 11B:
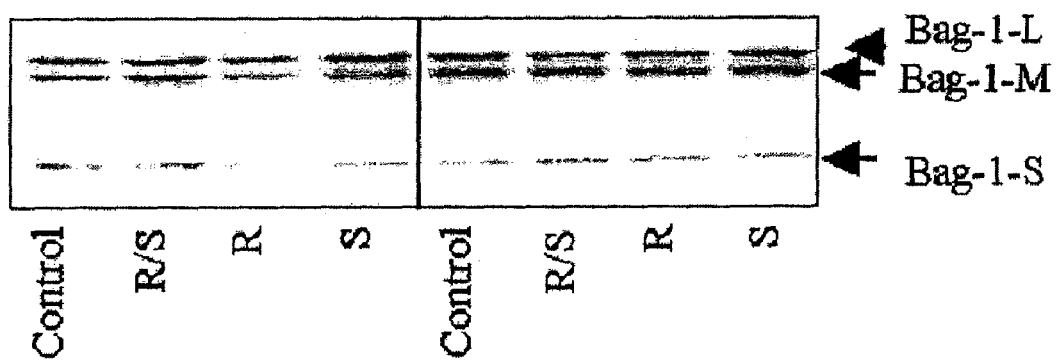

As planar hydrophobic compounds, etodolac and other NSAIDS can readily insert into cell and organ membranes, and can disrupt their structure and function (S. B. Abramson et al., *Arthritis and Rheumatism,* 32,1 (1989)). The proteins Mcl-1 and Bag-1 are anti-apoptotic members of the bcl-2 family that are found in mitochondria (X. Wang et al., *Exp. Cell Res.*, 235, 210 (1997)). As early as two hours after incubation with 100 µM etodolac, Mcl-1 and Bag-1 levels fell in an etodolac sensitive prostate cancer cell line (LNCaP). The fall in Mcl-1 and Bag-1 levels was prevented by co-incubation of the prostate cells with 5.0 µM MG-132, a recently described inhibitor of the proteasome (FIG. 11, Panels A and B, respectively) (D. H. Lee at al., *Trends Cell Biol.*, 8, 397 (1998)). Detergent lysates (20 µg per lane) were subjected to SDS-PAGE and immunoblotted with anti-Mcl-1 and anti-Bag-1 antibodies. Pre-incubation of the cells with Z-VAD, a broad-spectrum caspase inhibitor, did not prevent the Mcl-1 and Bag-1 downregulation. Etodolac incubation did not alter Bcl-2 and Bax levels (data not shown). Thus, etodolac did not interfere with Mcl-1 synthesis, but probably accelerated its turnover. Both R- and S-etodolac induced Mcl-1 degradation at equivalent concentrations.

EXAMPLE 22

Expression of PPAR-γ in Cancer Cell Lines

Figure 12:
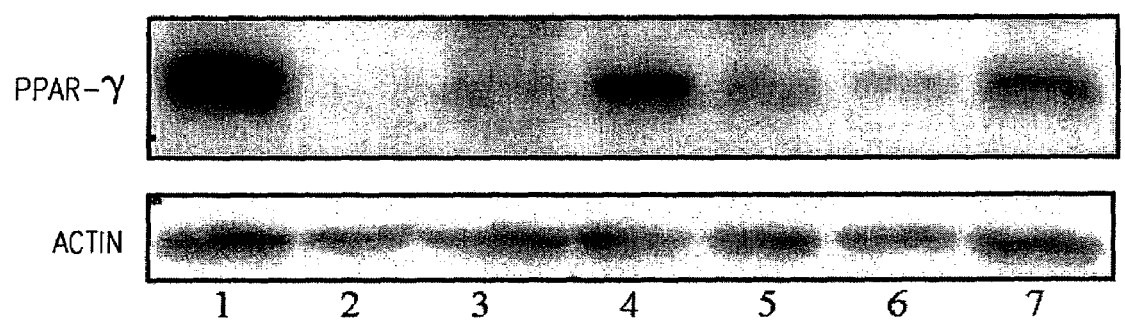
FIG. 12 is a photocopy of an SDS-PAGE gel depicting expression of PPAR-γ by seven cancer cell lines.

Although etodolac has not been previously studied, high concentrations of other NSAIDs have been reported to activate the nuclear hormone receptor PPAR-γ (J. M. Lehmann et al., *J. Biol. Chem.*, 272, 3406 (1997). Moreover, maximal activation of PPAR-γ induces apoptosis in human macrophages (G. Chinetti et al., *J. Biol. Chem.*, 273, 25579 (1998). Therefore, it was of interest to determine if prostate cells express PPAR-γ, and to compare the expression level with other cancer types. Detergent lysates (20 µg per lane) obtained from subconfluent cell lines were subjected to SDS-PAGE and immunoblotted with anti-PPAR-γ antibodies. To normalize the PPAR-γ content, the membrane was reblotted with an anti-actin monoclonal antibody. Lane 1: PC-3, Lane 2: SW260, Lane 3: A549, Lane 4: MDA-MB-231, Lane 5: Alva-31, Lane 6: LNCaP, Lane 7: HCT-116 (see Table 1). It was observed that some etodolac-susceptible prostate cells (PC3 especially) expressed remarkably high levels of immunoreactive PPAR-γ (FIG. 12).

EXAMPLE 23

Activation of PPAR-γ by Etodolac

Figure 13:
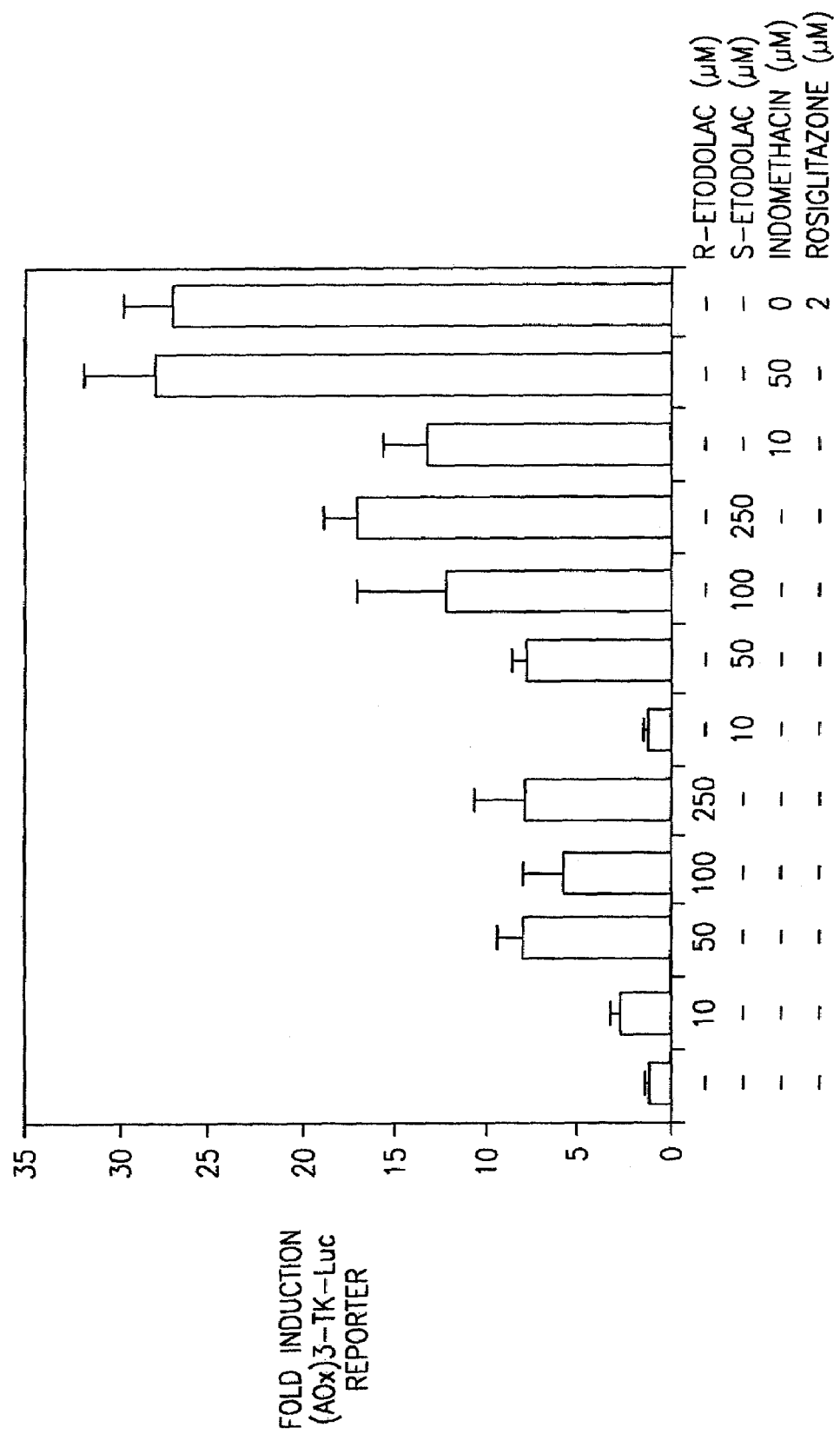
FIG. 13 is a graph depicting induction of PPAR-γ expression by etodolac and indomethacin.
Figure 14:
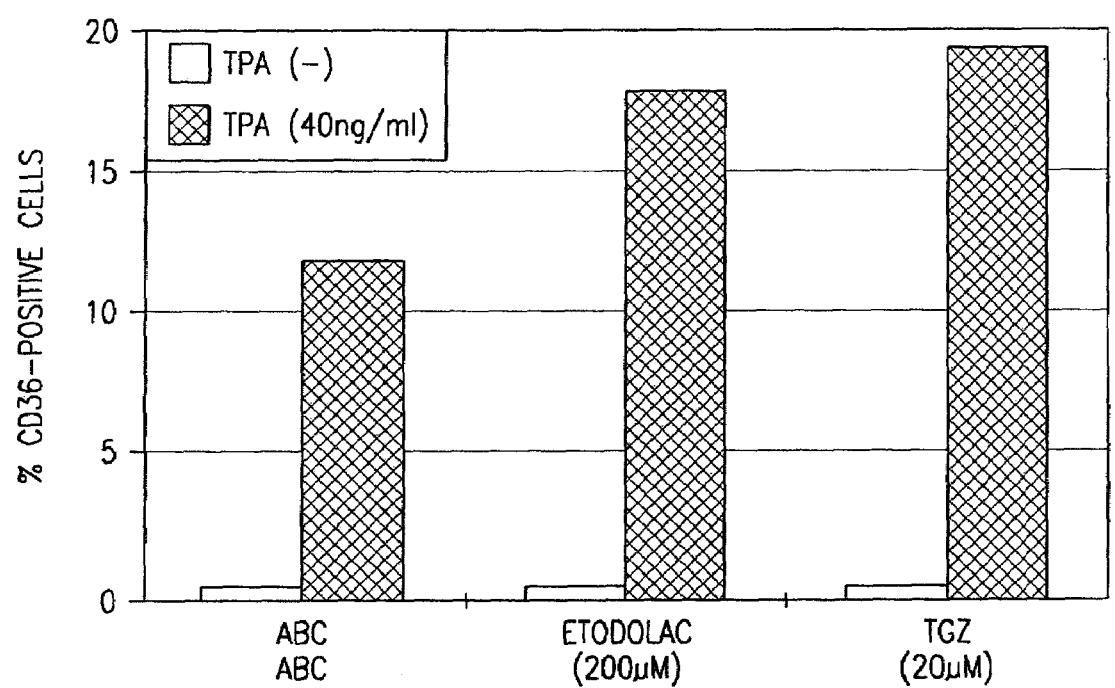
FIG. 14 is a graph depicting expression of CD36 induced by etodolac and TGZ, in the presence and absence of TPA in human monocytes.

RAW264.7 cells were transfected at a density of $3 \times 10^5$ cells/ml in six well plates using lipofectamine with the PPAR-γ expression vector pCMX-PPAR-γ (0.1 µg), and the PPAR-γ reporter construct $(AOx)_3$-TK-Luc (1 µg) as previously described by M. Ricote et al., *Nature*, 391, 79 (1998). Cells were treated for 24 hours with the compounds indicated on FIG. 13, harvested and assayed for luciferase activity. Results are expressed as the mean ±SD. As shown in FIG. 13, both the R- and S-enantiomers of etodolac activated a PPAR-γ reporter gene construct at concentrations readily achieved in human plasma after in vivo administration. THP-1 human monocytic cells (ATCC) were incubated in the presence or absence of phorbol ester (40 ng TPA) and 200 µM racemic etodolac or 20 µM troglitazone. After three days of culture, the surface expression of the scavenger receptor CD36 was measured by flow cytometry. As shown in FIG. 14, both R- and S-etodolac caused the expression of CD36, a marker of PPAR-γ activation, in the human cell line THP-1 during macrophage differentiation.

EXAMPLE 24

Etodolac Treatment of Prostate Cancer Tissue Samples

Figure 15:
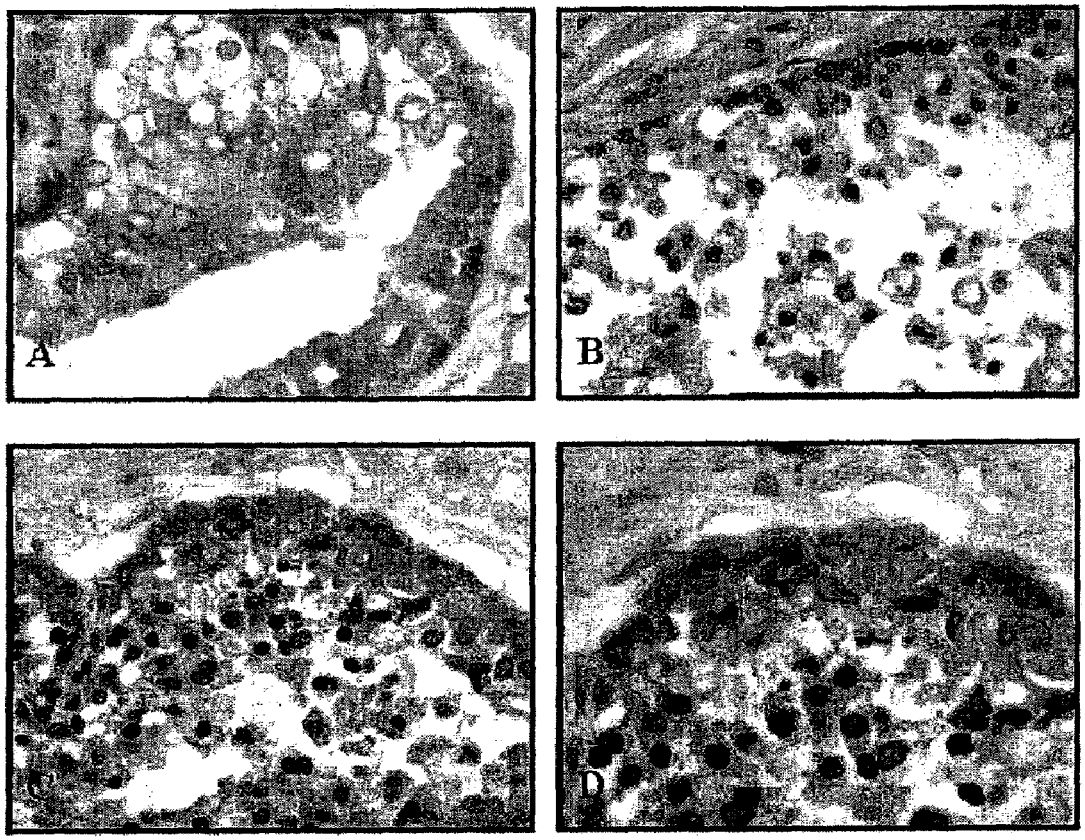
FIGS. 15A-15D are a copies of sections of prostate cancer tissue, untreated (A) or treated (B, C, D) with etodolac.

Freshly obtained prostatectomy samples were cut into 3 mm³ pieces, and incubated for 72 hours in RPMI-1640 supplemented with 10% FBS and antibiotics in the absence (A, 400×) or presence of racemic etodolac (B, 400×) or the purified R enantiomer (C, 400×; and D, 630×). The tissues were next fixed in 4% paraformaldehyde in PBS, embedded in paraffin, sectioned and stained with hematoxylin and eosin. FIG. 15A shows the infiltrating tumor cells (large nuclei) and some residual normal epithelium. FIGS. 15 B to 15 D show the effect of etodolac: note the abundant presence of pyknotic apoptotic nuclei (dark arrows, B and D), and the disintegration of the neoplastic glandular architecture (B+C). Etodolac was found to be selectively toxic to the tumor cells, but did not affect normal basal cells. The racemic mixture (R/S) and the purified R and S analogs were found both active.

EXAMPLE 25

Apoptotic Assays

The compounds of the invention were screened for CLL apoptotic activity by flow cytometry and a MTT-based assay. Primary CLL cells isolated from patients were used in both studies. Primary CLL cells were kindly provided by Dr. Thomas Kipps, University of California at San Diego, La Jolla, Calif. Primary PBL cells were acquired from the San Diego Blood Bank, San Diego, Calif. $DiOC_6$ and PI dyes were obtained from Molecular Probes, Eugene, Oreg. Otherwise, unless indicated, all other reagents were purchased from Sigma (St. Louis, Mo.), and all test compounds were dissolved in sterile DMSO.

Flow Cytometry Studies

Figure 16:
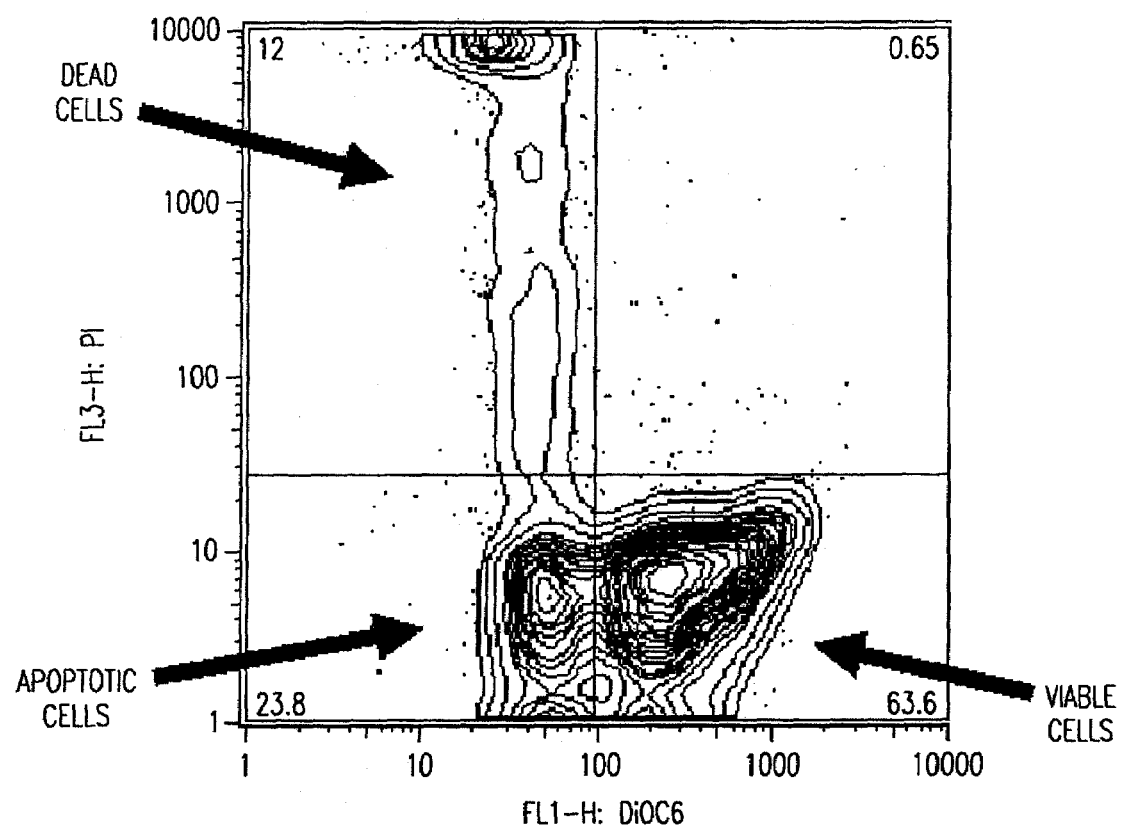
FIG. 16 is a graph depicting the detection of viable, apoptotic, and dead cells by flow cytometry using $DiOC_6$ and PI staining.

In the flow cytometry experiment, the cells were incubated with individual test compounds and stained with 3,3'-dihexyloxacarbocyanine iodide ($DiOC_6$), a cationic dye attracted to the mitochondrial transmembrane potential, and propidium iodide (PI), a membrane-impermeable nucleic acid dye. Viable cells ($DiOC_6^+$, $PI^-$) with functional mitochondria and an intact cell membrane retained $DiOC_6$ and excluded PI. In contrast, apoptotic cells ($DiOC_6^-$, $PI^-$) failed to absorb $DiOC_6$ because of their reduced mitochondrial potential resulting from apoptosis. The results were determined using the techniques of Zamzami, N., et al., *J Exp Med.*, 1995, 118, 1661-1672. Dead cells ($DiOC_6^-$, $PI^+$) took in PI after their outer cell membrane deteriorated. Dye absorption and the percentages of each cell type were then determined on a flow cytometer. (FIG. 16) The population of viable cells was used to estimate the effective concentration of each compound needed to cause apoptosis in 50% of CLL cells ($EC_{50}$). This experiment was then repeated with normal peripheral blood lymphocyte (PBL) cells to estimate the lethal concentration of each compound needed to kill 50% of normal cells ($LC_{50}$). Four drug levels (100, 250, 500, and 750 μM) were tested. Thus, most of the $EC_{50}$'s and $LC_{50}$'s were expressed as a range.

In each well of a 24-well plate, test compounds were added to 5×10⁶ primary CLL or PBL cells suspended in 2 mL of RPMI-1620 medium (Irvine Scientific, Santa Ana, Calif.) containing 10% fetal bovine serum (FBS), 100 μg/mL penicillin, and 100 μg/mL streptomycin to get final concentrations of 100, 250, 500, and 750 μM. Cells alone and R-etodolac served as controls. The plate was then incubated under a 5% $CO_2$ atmosphere at 37° C. for 48 hours, after which 450 μL of each well was removed, incubated for 30 minutes with 50 μL of phosphate buffer solution (PBS) containing 40 nM $DiOC_6$ and 5 μg/mL PI, and analyzed by flow cytometry using a FACS caliber (Beckton-Dickinson, San Jose, Calif.). Viable cells had high $DiOC_6$ and low PI signal. Early apoptotic cells had low signals of $DiOC_6$ and PI. Dead cells had low $DiOC_6$ and high PI signal. The results are illustrated in Table 2 and FIG. 16.

MTT Cytotoxicity Studies

To get a more concise measure of the $EC_{50}$ and confirm the flow cytometry results, a MTT (3-(4,5-dimethylthiazol-2-yl)-2,5-diphenyl tertrazolium bromide) assay using a procedure similar to that described by Mosmann, T., *J Immunol Methods*. 1983, 65, 55-63, was performed on all analogs. This method provided a larger number of datapoints so that a value for the $EC_{50}$ could be extrapolated.

This assay was based on a procedure described by Mosmann. Briefly, in each well of a 96-well plate, 5×10⁵ CLL cells were suspended in 100 μL of RPMI-1620 medium containing 10% FBS, 100 μg/mL penicillin, and 100 μg/mL streptomycin. Serial dilution of test compounds were then performed in duplicate across the plate to establish a concentration gradient from 0 to 1000 μM. After 72 hours of incubation at 37° C., the cells were incubated for 6 more hours in the presence of 20 μL of 5 mg/mL MTT (3-(4,5-dimethylthiazol-2-yl)-2,5-diphenyl tertrazolium bromide) before dissolving the resulting crystals in 50 μL lysis buffer (15% SDS, 15 mM HCl) overnight. Afterwards, the absorbance of each well was measured at 570 and 650 nM in a Finstrument Microplate Reader, and the data was analyzed by Graphpad Prism Software, version 2.0b. The results are illustrated in Table 2.

TABLE 2

$EC_{50}$ and $LC_{50}$ of the etodolac derivatives in CLL cells.

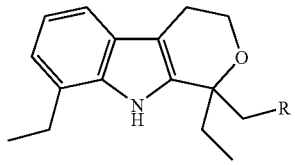

| | | MTT[a] | Flow Cytometry | |
|---|---|---|---|---|
| Compound | R | $EC_{50}$ (μM) | $EC_{50}$ (μM) | $LC_{50}$ (μM) |
| R-etodolac | COOH | 247.4 | 100-250 | ~500 |
| 1 | $CH_2OH$ | 177.5 | 100-250 | ~500 |
| 2 | $CH_2OCH_3$ | >1000 | 250-500 | >750 |
| 3 | $CH_2F$ | 767.3 | 250-500 | <100 |
| 4 | $CH_2Cl$ | 572.2 | <100 | <100 |
| 5 | $CH_3$ | >1000 | 250-500 | nd |
| 6 | $CONH_2$ | 257.9 | 100-250 | >500 |
| 7 | CH=NH | 714.1 | 250-500 | 250-500 |
| 8 | CHO | 111.3 | <100 | <100 |
| 9 | $CH_2OCH_2SCH_3$ | 324.5 | ~250 | nd |
| 10 | $CH_2OAc$ | 686.3 | 250-500 | 100-250 |
| 11 | $CH(OH)_2$ | 415.8 | 250-500 | nd |
| 12 | $CHOHCH_3$ | 272.4 | 100-250 | 250-500 |
| 13 | $COCH_3$ | >1000 | 250-500 | >750 | nd = not determined
[a]Assays were performed in duplicate.

Activity Screening Assays

Normal prostate cells (PREC, Cambrex East Rutherford N.J.), prostate cell line (LnCAP, ATCC, Manassas, Va., USA), myeloma cell line (RPMI-8226, ATCC, Manassas, Va., USA), PBL (peripheral blood leukocytes-buffy coat San Diego Blood Bank), and primary CLL cells were incubated for one to two days in RPMI-1640 and 10% FBS (fetal bovine serum). They were plated in 96-well plates at 100,000 cells/well. Titrated concentrations of the compound to be tested were added to the culture medium. The cells were incubated three days at 37° C., 5% $CO_2$. Viability of the cells was assayed by standard MTT assay. Each drug concentration was done in duplicate. The results are illustrated in Table 3.

TABLE 3

| Compound | Structure | MW | CLL (μm) by MTT | LnCap (μM) | RPMI-8226 (μM) |
|---|---|---|---|---|---|
| (R-Etodolac) | 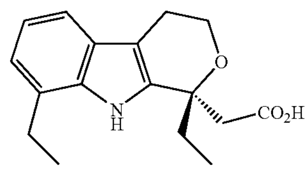 | 287.36 | 174.1 (1st) 263.1 (2nd) | 95 (1st) 132.0 (2nd) 140 (3rd) 108.4 (4th) | 250 (1st) 197.3 (2nd) 250 (3rd) 139.4 (4th) |
| 1 | 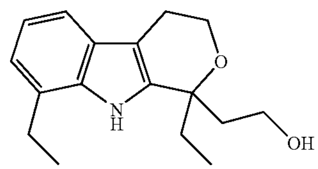 | 273.37 | 177.4 | 39.8 | 134.7 |
| 2 | 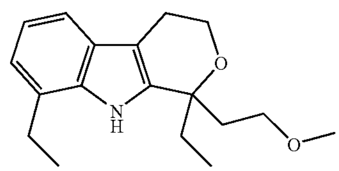 | 287.40 | >1000 | | 473.5 |
| 3 | 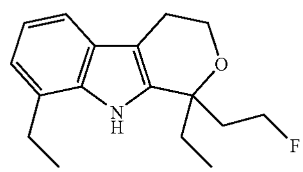 | 275.37 | 767.3 | ~210 | ~190 |
| 4 | 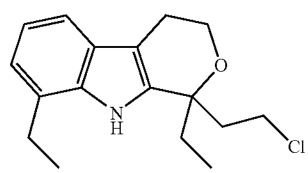 | 291.82 | 572.2 | ~58 | ~105 |
| 5 | 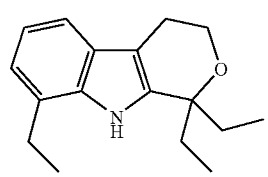 | 257.38 | >1000 | 340 | ~180 |
| 6 | 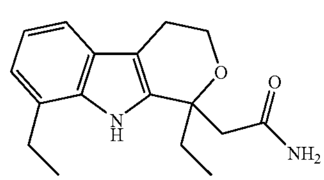 | 286.37 | 105 200 190 160 160 | 59.6 | 109.6 |

TABLE 3-continued

| Compound | Structure | MW | CLL (µm) by MTT | LnCap (µM) | RPMI-8226 (µM) |
|---|---|---|---|---|---|
| 7 | 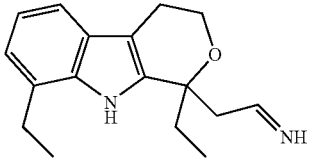 | 270.37 | 714.3 | ~100 | ~270 |
| 8 | 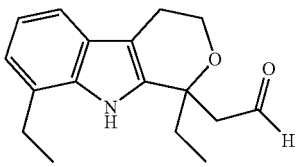 | 271.36 | 111.3 | 57 | ~70 uM |
| 9 | 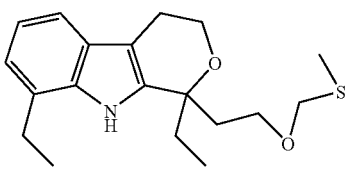 | 333.49 | 324.5 | ~140 | 121.5 |
| 10 | 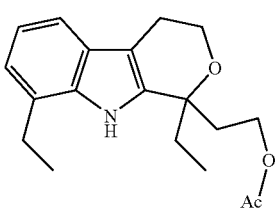 | 315.41 | 686.3 | | |
| 11 | 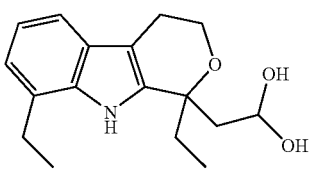 | 289.38 | 415.8 | 200.9 | 304.9 |
| 12 | 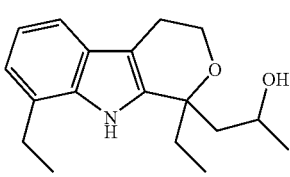 | 287.40 | 272.4 | 62.7 | ~110 |
| 13 | 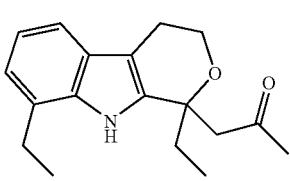 | 285.39 | 686.3 | 39.8 | 53.3 |

COX-1/COX-2 Enzyme Assays

Compounds active in both the flow cytometry and MTT experiments were then tested for COX inhibition at 50 µM in an enzyme assay using COX-1 isolated from human platelets and human recombinant COX-2 purified from insect cells (*Spodoptera frugiperda*), as described by Riendeau et. al., *Br J Pharmacol.* 1997, 121, 105-117; Riendeau et. al., *Can J Physiol Pharmacol.* 1997, 75, 1088-1095; and Warner et. al. *Proc Natl Acad Sci.* 1999, 96, 7563-7568. These assays were performed by MDS Pharma Services, Bothell, Wash. The compounds were incubated in duplicate with COX-1 isolated from human platelets and human recombinant COX-2 purified from insect cells (*Spodoptera frugiperda*). Enzyme immunoassay quantification of prostaglandin $E_2$ production from arachidonic acid in the presence (50 µM) and absence of test compounds was used to determine the percentage of COX inhibition. The results are illustrated in Table 4.

TABLE 4

COX Inhibition of Compound 1 and 6.

| Compound | R | % Inhibition[a] | |
|---|---|---|---|
| | | COX-1 | COX-2 |
| 1 | CH$_2$OH | 0 | 0 |
| 6 | CONH$_2$ | 36 | 69 |

[a]Percentages of inhibition of COX-1 isolated from human platelets and purified human recombinant COX-2. Compounds were tested at 50 μM. Assays were performed in duplicate.

All of the publications and patent documents cited hereinabove are incorporated by reference herein. The invention has been described with reference to various specific and preferred embodiments and techniques. However, it should be understood that many variations and modifications may be made while remaining within the spirit and scope of the invention.

What is claimed is:

1. A method of treating prostate cancer in a patient in need thereof comprising administering to said patient an effective amount of a compound of formula (I):

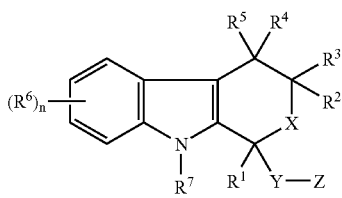

(I)

wherein R$^1$ is lower alkyl, lower alkenyl, lower alkynyl, phenyl, benzyl or 2-thienyl, R$^2$, R$^3$, R$^4$ and R$^5$ are the same or different and are each hydrogen or lower alkyl;

each R$^6$ is individually hydrogen, lower alkyl, hydroxy, (hydroxy)lower alkyl, lower alkoxy, benzyloxy, lower alkanoyloxy, nitro or halo, n is 1-3, R$^7$ is hydrogen, lower alkyl or lower alkenyl, X is oxy or thio, Y is (CH$_2$)$_{1-3}$, (CH$_2$)$_{1-3}$SO$_2$ or (CH$_2$)$_{1-3}$C(O), and Z is (ω-(4-pyridyl)(C$_2$-C$_4$alkoxy), (ω-((R$^8$)(R$^9$)amino)(C$_2$-C$_4$ alkoxy), an amino acid ester of (ω-(HO)(C$_2$-C$_4$))alkoxy, N(R$^8$)CH(R$^8$)CO$_2$H, 1'-D-glucuronyloxy, OH, (C$_2$-C$_4$)acyloxy, SO$_3$H, PO$_4$H$_2$, N(NO)(OH), SO$_2$NH$_2$, PO(OH)(NH$_2$), OCH$_2$CH$_2$N(CH$_3$)$_3$$^+$, amino, lower alkylamino, di(lower alkyl)amino, phenylamino, or tetrazolyl;

wherein R$^8$ and R$^9$ are each H, (C$_1$-C$_3$)alkyl or together with N, are a 5- or 6-membered heterocyclic ring having 1-3 N(R$^8$), S or nonperoxide O; or Y-Z is (CH$_2$)$_{1-3}$R$^{10}$ wherein R$^{10}$ is OH, (C$_2$-C$_4$)acyloxy, SO$_3$H, PO$_4$H$_2$, N(NO)(OH), SO$_2$NH$_2$, PO(OH)NH$_2$.

2. The method of claim 1 wherein Y-Z is a pyridylalkyl ester, a morpholinoalkyl ester, an aminoalkyl ester or a hydroxyalkyl ester.

3. The method of claim 1 wherein Y-Z is a glucamine ester or N—(C$_1$-C$_4$)alkyl-glucamine ester of CH$_2$CO$_2$H.

4. The method of claim 1 wherein Y is —CH$_2$— and Z is —CHO, —CH$_2$OH, —CONH$_2$, —CHOHCH$_3$, —CH$_2$OCH$_2$SCH$_3$, or —CH(OH)$_2$.

5. The method of claim 1 wherein Y-Z is the 1'-D-glucuronate ester of CH$_2$CO$_2$H, a water-soluble amide of CH$_2$CO$_2$H, or an amino acid amide of CH$_2$CO$_2$H.

* * * * *